(12) United States Patent
Wang et al.

(10) Patent No.: US 9,382,591 B2
(45) Date of Patent: Jul. 5, 2016

(54) **COMPOSITIONS FOR DETECTING *ALICYCLOBACILLUS* MICROORGANISMS**

(71) Applicant: Pall Corporation, Port Washington, NY (US)

(72) Inventors: Yu Wang, North Grafton, MA (US); Yun Bao, Fremont, CA (US)

(73) Assignee: PALL CORPORATION, Port Washington, NY (US)

( * ) Notice: Subject to any disclaimer, the term of this patent is extended or adjusted under 35 U.S.C. 154(b) by 370 days.

(21) Appl. No.: 13/911,733

(22) Filed: Jun. 6, 2013

(65) Prior Publication Data
US 2014/0363811 A1    Dec. 11, 2014

(51) Int. Cl.
*C12Q 1/68* (2006.01)

(52) U.S. Cl.
CPC .......... *C12Q 1/689* (2013.01); *C12Q 2600/156* (2013.01)

(58) Field of Classification Search
None
See application file for complete search history.

(56) References Cited

U.S. PATENT DOCUMENTS

| 6,821,771 | B2 | 11/2004 | Festoc |
| 2004/0265850 | A1 | 12/2004 | Wang et al. |
| 2006/0216720 | A1 | 9/2006 | Carvalho et al. |
| 2007/0207458 | A1 | 9/2007 | Nakakita et al. |
| 2007/0212715 | A1 | 9/2007 | Yamanaka et al. |
| 2008/0026368 | A1* | 1/2008 | Snaidr .................. C12Q 1/6895 435/134 |
| 2009/0226886 | A1 | 9/2009 | Mitsuhashi |
| 2011/0065110 | A1 | 3/2011 | Isac et al. |
| 2012/0088680 | A1 | 4/2012 | Robison et al. |

FOREIGN PATENT DOCUMENTS

| EP | 1 273 668 A1 | 1/2003 |
| EP | 1 672 081 A1 | 6/2006 |
| EP | 1 788 093 A1 | 5/2007 |
| JP | 2011-509669 A | 3/2011 |
| WO | 2004/063699 A2 | 7/2004 |
| WO | 2005/031004 A2 | 4/2005 |

OTHER PUBLICATIONS

Connor et al. (International Journal of Food Microbiology 99 (2005) 229-235).*
GenBank AB042055, *Alicyclobacillus herbarius* gene for 16S ribosomal RNA, partial sequence, Jun. 14, 2007, 1 page.*
Vernet et al. (Journal of Applied Microbiology 2004, 96, 59-68).*
Yakoubou et al. (Natural Science, vol. 2, No. 9, 990-997 (2010)).*
Goto et al., "*Alicyclobacillus acidoterrestris* gene for 16S rRNA, strain:DSM 3924," GenBank AB059676 (2009).
Partial European Search Report, Applcation No. 14170880, dated Oct. 28, 2014.
Postollec et al., "A multiparametric PCR-based tool for fast detection and identification of spore-forming bacteria in food," *Intl. J. of Food Microbiol.*, 142, 78-88 (2010).
Connor, C. J. et al., "Development of a real-time PCT-based system targeting the 16S rRNA gene sequence for rapid detection of *Alicyclobacillus* spp. in juice products," *Int. J. Food Microbiol.*, 99, 229-235 (2005).
Gouws, P. A. et al., "Isolation and identification of *Alicyclobacillus acidocaldarius* by 16S rDNA from mango juice and concentrate," *Int. J. Food Sci. Tech.*, 40(7), 789-792 (2005).
Luo, H. et al., "A real-time polymerase chain reaction-based method for rapid and specific detection of spoilage *Allcyclobacillus* spp. in apple juice," *Lett. Appl. Microbiol.*, 39, 376-382 (2004).
Yamazaki, K. et al., "Specific primers for detection of *Alicycobacillus acidoterrestris* by RT-PCT," *Lett. Appl. Microbiol.*, 23(5), 350-354 (1996).
Search Report, Singapore Application No. 10201402775Q mailed Oct. 10, 2014.
"*Alicyclobacillus* Detection Kit," *Biotecon Diagnostics*, http://bc-diagnostics.com/?cid=1310390272&name=Alicyclobacillus+Detection+Kit, Retrieved on May 2, 2013.
"Detection of *Alicyclobacillus* in Beverages," *rapidmicrobiology*, http://www.rapidmicrobioloy.com/test-methods/Alicyclobacillus.php, Retrieved on May 2, 2013.

* cited by examiner

*Primary Examiner* — Juliet Switzer
(74) *Attorney, Agent, or Firm* — Leydig, Voit & Mayer Ltd.

(57) ABSTRACT

The invention provides nucleic acids, collections of nucleic acids, supports, assay kits, and methods for the sensitive and specific detection of microorganisms in a foodstuff. The nucleic acid comprises a nucleotide sequence selected from the group consisting of SEQ ID NOs: 1-15 and having a length of no more than 35 nucleotides.

19 Claims, No Drawings

US 9,382,591 B2

COMPOSITIONS FOR DETECTING *ALICYCLOBACILLUS* MICROORGANISMS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 13,658 Byte ASCII (Text) file named "712628ST25.TXT," dated Jun. 4, 2013.

BACKGROUND OF THE INVENTION

Microorganisms (e.g., bacteria) may cause the spoilage of foodstuffs (e.g., fruit juice) during or after manufacture. Some microorganisms may cause foodstuff spoilage and any one or more of several undesirable effects such as, for example, unpleasant odor, unpleasant taste, and rendering the foodstuff unsafe for consumption. Failure to accurately and rapidly detect the presence of foodstuff-spoiling microorganisms may increase the risk of food spoilage. Obstacles to the rapid and accurate detection of the microorganisms that cause the spoilage of foodstuffs may include, for example, the lengthy duration of the traditional microbiology methods used to detect the microorganisms. These traditional methods may take an average of 10-12 days to complete. Another obstacle to accurate detection may include, for example, the similarity of the genomic sequences of some foodstuff-spoiling microorganisms as compared to that of non-foodstuff-spoiling microorganisms.

Accordingly, there is a need for improved compositions and methods for detecting microorganisms that cause the spoilage of foodstuffs.

BRIEF SUMMARY OF THE INVENTION

An embodiment of the invention provides a nucleic acid comprising a nucleotide sequence selected from the group consisting of SEQ ID NOs: 1-15 and having a length of no more than 35 nucleotides.

Another embodiment of the invention provides a collection of nucleic acids comprising two or more nucleic acids, wherein each nucleic acid comprises a nucleotide sequence selected from the group consisting of SEQ ID NOs: 1-15 and has a length of no more than 35 nucleotides.

Still another embodiment of the invention provides a support comprising the inventive nucleic acid or collection of nucleic acids immobilized on the support.

Another embodiment of the invention provides a method of detecting the presence of one or more *Alicyclobacillus* microorganisms in a foodstuff, the method comprising: (a) obtaining at least one test sample comprising isolated microorganism nucleic acid from foodstuff; (b) contacting any of the inventive nucleic acids, collections of nucleic acids, or supports described herein with the at least one test sample under conditions allowing for a complex to form between the nucleic acid and the microorganism nucleic acid; (c) detecting the complex; and (d) comparing a presence of the complex in the at least one test sample with an absence of complex from a negative sample that lacks microorganism nucleic acid, wherein detection of the complex is indicative of the presence of one or more *Alicyclobacillus* microorganisms.

A preferred embodiment of the invention provides a method of detecting the presence of one or more foodstuff-spoiling *Alicyclobacillus* microorganisms in a foodstuff, the method comprising: (a) obtaining at least one test sample comprising isolated microorganism nucleic acid from foodstuff; (b) contacting any of the inventive nucleic acids, collections of nucleic acids, or supports described herein with the at least one test sample under conditions allowing for a complex to form between the nucleic acid and the microorganism nucleic acid; (c) detecting the complex; and (d) comparing a presence of the complex in the at least one test sample with an absence of complex from a negative sample that lacks microorganism nucleic acid, wherein detection of the complex is indicative of the presence of one or more foodstuff-spoiling *Alicyclobacillus* microorganisms.

DETAILED DESCRIPTION OF THE INVENTION

An embodiment of the invention provides a nucleic acid comprising a nucleotide sequence selected from the group consisting of SEQ ID NOs: 1-15 and having a length of no more than 35 nucleotides. In an embodiment of the invention, the nucleotide sequence may comprise additional nucleotides up to a length of no more than 35 nucleotides. In this regard, an embodiment of the invention provides a nucleotide sequence selected from the group consisting of SEQ ID NOs: 31-74 and having a length of no more than 35 nucleotides. In still another embodiment of the invention, the nucleic acid comprises a nucleotide sequence selected from the group consisting of SEQ ID NOs: 16-30 and having a length of no more than 35 nucleotides. The nucleic acid may have any suitable length that is no more than 35 nucleotides. For example, the nucleic acid may have a length of no more than 34, 33, 32, 31, 30, 29, 28, 27, 26, 25, 24, 23, 22, 21, 20, 19, 18, 17, 16, or 15 nucleotides. In still another embodiment of the invention, the nucleic acid may consist of a nucleotide sequence selected from the group consisting of SEQ ID NOs: 1-74.

In an embodiment, the nucleic acid is isolated or purified. The inventive nucleic acids provide forward primers, reverse primers, and probes which may, advantageously, specifically hybridize with a microorganism nucleic acid for detection of the presence of one or more microorganisms in a foodstuff. In some embodiments, the primers and probes specifically hybridize with the nucleic acid of multiple species within a specific genus of microorganisms (hereinafter, "genus-specific nucleic acids"). In other embodiments, the primers and probes specifically hybridize with the nucleic acid of a specific species of microorganism (hereinafter, "species-specific nucleic acids").

The inventive genus-specific nucleic acids may be used to detect the presence of one or more microorganisms that may or may not cause foodstuff spoilage in a sample of foodstuff. In an embodiment of the invention, the inventive genus-specific nucleic acids may specifically detect the presence of two or more of any of a variety of different species of microorganisms within the genus *Alicyclobacillus*. The number of *Alicyclobacillus* species detected by the inventive genus-specific nucleic acids is not limited and may include, for example, 2, 3, 4, 5, 6, 7, 8, 9, 10, 11, 12, 13, 14, 15, 16, 17, 18, 19, 20, 21, 22, 23, or more *Alicyclobacillus* species. The number of *Alicyclobacillus* strains detected by the inventive genus-specific nucleic acids is not limited and may include, for example, 10, 20, 30, 40, 50, 60, 70, 80, 90, 100, 110, 120, 130, 140, 150, 160, 170, 180, 190, 200, or more *Alicyclobacillus* strains. Exemplary species of microorganisms specifically detectable by the inventive genus-specific nucleic acids include any one or more of *Alicyclobacillus acidocaldarius, Alicyclobacillus contaminans, Alicyclobacillus disulfidooxidans, Alicyclobacillus fastidiosus, Alicyclobacillus ferrooxydans, Alicyclobacillus hesperidum, Alicyclobacillus* pomorum, Alicyclobacillus sacchari, Alicyclobacillus sendaiensis, Alicyclobacillus shizuokensis, Alicyclobacillus tolerans, Alicyclobacillus vulcanalis, Alicyclobacillus tengchongenesis, Alicyclobacillus acidoterrestris, Alicyclobacillus acidiphilus, Alicyclobacillus cycloheptanicus, and Alicyclobacillus herbarius. In a preferred embodiment, the inventive genus-specific nucleic acids specifically detect any one or more of Alicyclobacillus acidoterrestris, Alicyclobacillus acidiphilus, Alicyclobacillus cycloheptanicus, and Alicyclobacillus herbarius. In an embodiment of the invention, the genus-specific nucleic acids may comprise or consist of a nucleotide sequence selected from the group consisting of SEQ ID NOs: 1-3, 16-18, and 31-41.

The inventive species-specific nucleic acids may be used to detect the presence of one or more microorganisms that cause spoilage in a sample of foodstuff. In an embodiment of the invention, the inventive nucleic acids may specifically detect the presence of any one or more of a variety of different species of microorganisms within the genus Alicyclobacillus that cause spoilage in a sample of foodstuff. Exemplary species of microorganisms that cause spoilage in a sample of foodstuff that are specifically detectable by the inventive nucleic acids include any one or more of Alicyclobacillus acidoterrestris, Alicyclobacillus acidiphilus, Alicyclobacillus cycloheptanicus, and Alicyclobacillus herbarius. In an embodiment of the invention, the species-specific nucleic acids may comprise or consist of a nucleotide sequence selected from the group consisting of SEQ ID NOs: 4-15, 19-30, and 42-74. The inventive genus-specific and species-specific nucleic acids, and the exemplary species of microorganisms specifically detectable by the inventive nucleic acids, are set forth in Tables 1-4.

TABLE 1

| Species | Type | Sequence | SEQ ID NO |
|---|---|---|---|
| Alicyclobacillus spp. (genus-specific) | Forward Primer | TGGACAGTGACTGAC | 1 |
| | Reverse Primer | GCTTATTGGGTTTCC | 2 |
| | Probe | CGTAAACGATGAGTG | 3 |
| Alicyclobacillus acidoterrestris | Forward Primer | AATCTGCCTTTCAGA | 4 |
| | Reverse Primer | TCTTTCAACACAAAT | 5 |
| | Probe | ATTATCCGGCATTAG | 6 |
| Alicyclobacillus acidiphilus | Forward Primer | CGTTGTCCGGAATCA | 7 |
| | Reverse Primer | GTTTCCAAAGACAAA | 8 |
| | Probe | ACTTACACAACCGCC | 9 |
| Alicyclobacillus cycloheptanicus | Forward Primer | TGGGAAAGGTGCAAG | 10 |
| | Reverse Primer | TCGTCGCCTTGGTGA | 11 |
| | Probe | CGCAGATGGAGGAGC | 12 |
| Alicyclobacillus herbarius | Forward Primer | ACACCACGAGAGTGA | 13 |
| | Reverse Primer | GCGGCTGGCTCCTAT | 14 |
| | Probe | CGAAGTCGGTGAGGC | 15 |

TABLE 2

| Species | Type | Sequence | SEQ ID NO |
|---|---|---|---|
| Alicyclobacillus spp. | Forward Primer | CTTGCTGGACAGTGACTGAC | 16 |
| | Reverse Primer | CCCGGAGTGCTTATTGGGTTTCC | 17 |
| | Probe | CCACGCCGTAAACGATGAGTGCTAGGTG | 18 |
| Alicyclobacillus acidoterrestris | Forward Primer | GGGGCAATCTGCCTTTCAGA | 19 |
| | Reverse Primer | CAGTTGCATCTTTCAACACAAAT | 20 |
| | Probe | CCCGTGTATTATCCGGCATTAGCACCCGT | 21 |
| Alicyclobacillus acidiphilus | Forward Primer | CGCAAGCGTTGTCCGGAATCA | 22 |
| | Reverse Primer | AAGTTATGCAGTTTCCAAAGACAAA | 23 |
| | Probe | ACTCCAGACTTACACAACCGCCTACGCA | 24 |
| Alicyclobacillus cycloheptanicus | Forward Primer | GCTGGGAAAGGTGCAAG | 25 |
| | Reverse Primer | GGCATCGTCGCCTTGGTGA | 26 |
| | Probe | CACCGCAGATGGAGGAGCCCGC | 27 |

TABLE 2-continued

| Species | Type | Sequence | SEQ ID NO |
|---|---|---|---|
| Alicyclobacillus herbarius | Forward Primer | GTCACACCACGAGAGTGA | 28 |
| | Reverse Primer | CGGGCGGCTGGCTCCTAT | 29 |
| | Probe | ACACCCGAAGTCGGTGAGGCAACCG | 30 |

TABLE 3

| Species | Type | Sequence | SEQ ID NO |
|---|---|---|---|
| Alicyclobacillus spp. | Forward Primers | TTGCTGGACAGTGACTGAC | 31 |
| | | TGCTGGACAGTGACTGAC | 32 |
| | | GCTGGACAGTGACTGAC | 33 |
| | | CTGGACAGTGACTGAC | 34 |
| | Reverse Primers | CCGGAGTGCTTATTGGGTTTCC | 35 |
| | | CGGAGTGCTTATTGGGTTTCC | 36 |
| | | GGAGTGCTTATTGGGTTTCC | 37 |
| | | GAGTGCTTATTGGGTTTCC | 38 |
| | | AGTGCTTATTGGGTTTCC | 39 |
| | | GTGCTTATTGGGTTTCC | 40 |
| | | TGCTTATTGGGTTTCC | 41 |
| Alicyclobacillus acidoterrestris | Forward Primers | GGGCAATCTGCCTTTCAGA | 42 |
| | | GGCAATCTGCCTTTCAGA | 43 |
| | | GCAATCTGCCTTTCAGA | 44 |
| | | CAATCTGCCTTTCAGA | 45 |
| | Reverse Primers | AGTTGCATCTTTCAACACAAAT | 46 |
| | | GTTGCATCTTTCAACACAAAT | 47 |
| | | TTGCATCTTTCAACACAAAT | 48 |
| | | TGCATCTTTCAACACAAAT | 49 |
| | | GCATCTTTCAACACAAAT | 50 |
| | | CATCTTTCAACACAAAT | 51 |
| | | ATCTTTCAACACAAAT | 52 |

TABLE 4

| Species | Type | Sequence | SEQ ID NO: |
|---|---|---|---|
| Alicyclobacillus acidiphilus | Forward Primers | GCAAGCGTTGTCCGGAATCA | 53 |
| | | CAAGCGTTGTCCGGAATCA | 54 |
| | | AAGCGTTGTCCGGAATCA | 55 |
| | | AGCGTTGTCCGGAATCA | 56 |
| | | GCGTTGTCCGGAATCA | 57 |
| | Reverse Primers | AGTTATGCAGTTTCCAAAGACAAA | 58 |
| | | GTTATGCAGTTTCCAAAGACAAA | 59 |
| | | TTATGCAGTTTCCAAAGACAAA | 60 |
| | | TATGCAGTTTCCAAAGACAAA | 61 |
| | | ATGCAGTTTCCAAAGACAAA | 62 |
| | | TGCAGTTTCCAAAGACAAA | 63 |
| | | GCAGTTTCCAAAGACAAA | 64 |
| | | CAGTTTCCAAAGACAAA | 65 |
| | | AGTTTCCAAAGACAAA | 66 |
| Alicyclobacillus cycloheptanicus | Forward Primer | CTGGGAAAGGTGCAAG | 67 |
| | Reverse Primers | GCATCGTCGCCTTGGTGA | 68 |
| | | CATCGTCGCCTTGGTGA | 69 |
| | | ATCGTCGCCTTGGTGA | 70 |
| Alicyclobacillus herbarius | Forward Primers | TCACACCACGAGAGTGA | 71 |
| | | CACACCACGAGAGTGA | 72 |
| | Reverse Primers | GGGCGGCTGGCTCCTAT | 73 |
| | | GGCGGCTGGCTCCTAT | 74 |

The nucleic acids of the invention provide many advantages. These advantages may include, for example, the rapid, sensitive, and specific detection of microorganisms. Combinations of the inventive nucleic acids may also provide for the detection of a larger number of species, including, e.g., four species, within the genus *Alicyclobacillus* that may cause spoilage as compared to the detection of one spoiler species using, e.g., commercially available quantitative polymerase chain reaction (qPCR)-based methods. The inventive nucleic acids may also provide for the detection of a larger number of strains, e.g., over 200 *Alicyclobacillus* strains, as compared to the detection of 38 *Alicyclobacillus* strains using, e.g., commercially available qPCR-based methods. An embodiment of the inventive nucleic acid also makes it possible to detect the presence of microorganisms within the genus *Alicyclobacillus* that may or may not cause spoilage, which, advantageously, provides a rapid and sensitive initial screening test to determine the presence of *Alicyclobacillus* microorganisms generally. This initial screening test may, advantageously, be employed prior to testing for the presence of specific species of *Alicyclobacillus* microorganisms that may cause spoilage. While the specific detection of those *Alicyclobacillus* species that cause spoilage can be challenging due to the high sequence similarities between spoiler *Alicyclobacillus* species and non-spoiler *Alicyclobacillus* species, embodiments of the inventive nucleic acids advantageously specifically detect *Alicyclobacillus* species that cause spoilage. Accordingly, the inventive nucleic acids advantageously make it possible to detect the presence of *Alicyclobacillus* microorganisms that may cause spoilage and avoid contamination and the development of off-flavors in foodstuff.

The inventive nucleic acids can specifically detect any type of nucleic acid of a microorganism. In an embodiment of the invention, the microorganism nucleic acid is DNA. In still another embodiment, the inventive nucleic acid is a nucleic acid consisting of a nucleotide sequence that is complementary to any of SEQ ID NOs: 1-74. The nucleic acid that is complementary to any of SEQ ID NOs: 1-74 may detect microorganism RNA.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the inventive nucleic acid further comprises a detectable label. The label may be any label suitable for detecting hybridization, e.g., a complex, of the inventive nucleic acid with microorganism nucleic acid. Exemplary detectable labels may include any one or more of radioactive labels, non-radioactive labels, fluorescent labels, and chemiluminescent labels.

Another embodiment of the invention provides a collection of nucleic acids comprising two or more of any of the nucleic acids described herein. In an embodiment of the invention, the collection may comprise or further comprise a nucleotide sequence complementary to any of the nucleic acids described herein. The collection may comprise any suitable number of inventive nucleic acids. For example, the collection may comprise from about 2 to about 75 or more nucleic acids, from about 10 or less to about 70 or more nucleic acids, from about 20 or less to about 60 or more nucleic acids, or from about 30 or less to about 50 or more nucleic acids. In this regard, the collection may comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, 61 or more, 62 or more, 63 or more, 64 or more, 65 or more, 66 or more, 67 or more, 68 or more, 69 or more, 70 or more, 71 or more, 72 or more, 73 or more, or 74 or more nucleic acids. Although the two or more nucleic acids of the collection may be identical to one another, in a preferred embodiment, the two or more nucleic acids are different from each other. Accordingly, the two or more different nucleic acids may, advantageously, hybridize with two or more different microorganism nucleic acids and, therefore, detect the presence of two or more different microorganisms in a foodstuff.

In an embodiment of the invention, the collection of nucleic acids includes a first nucleic acid and a second nucleic acid. The first nucleic acid may be any forward primer described herein and the second nucleic acid may be any reverse primer described herein. In this regard, the collection may comprise a first nucleic acid comprising a nucleotide sequence selected from the group consisting of SEQ ID NOs: 1, 4, 7, 10, 13, 16, 19, 22, 25, 28, 31-34, 42-45, 53-57, 67, and 71-72 and a second nucleic acid comprising a nucleotide sequence selected from the group consisting of SEQ ID NOs: 2, 5, 8, 11, 14, 17, 20, 23, 26, 29, 35-41, 46-52, 58-66, 68-70, and 73-74, wherein each of the two or more nucleic acids has a length of no more than 35 nucleotides. In an embodiment of the invention, the collection comprises nucleotide sequences comprising (a) SEQ ID NOs: 1-2; (b) SEQ ID NOs: 4-5; (c) SEQ ID NOs: 7-8; (d) SEQ ID NOs: 10-11; or (e) SEQ ID NOs: 13-14, wherein each of the two or more nucleic acids has a length of no more than 35 nucleotides. In another embodiment of the invention, the collection comprises nucleic acids consisting of (a) SEQ ID NOs: 16-17; (b) SEQ ID NOs: 19-20; (c) SEQ ID NOs: 22-23; (d) SEQ ID NOs: 25-26; or (e) SEQ ID NOs: 28-29. The nucleotide sequences of the collections described herein may have any suitable length as described herein with respect to other aspects of the invention.

In an embodiment of the invention, the first and second nucleic acids of the collection are both genus-specific nucleic acids. In this regard, both of the first and second nucleic acids of the collection may hybridize with two or more *Alicyclobacillus* species. In an embodiment, the collection may comprise a genus-specific collection comprising (1) SEQ ID NOs: 1 and 2, (2) SEQ ID NOs: 1 and 17, (3) SEQ ID NOs: 1 and 35, (4) SEQ ID NOs: 1 and 36, (5) SEQ ID NOs: 1 and 37, (6) SEQ ID NOs: 1 and 38, (7) SEQ ID NOs: 1 and 39, (8) SEQ ID NOs: 1 and 40, (9) SEQ ID NOs: 1 and 41, (10) SEQ ID NOs: 16 and 2, (11) SEQ ID NOs: 16 and 17, (12) SEQ ID NOs: 16 and 35, (13) SEQ ID NOs: 16 and 36, (14) SEQ ID NOs: 16 and 37, (15) SEQ ID NOs: 16 and 38, (16) SEQ ID NOs: 16 and 39, (17) SEQ ID NOs: 16 and 40, (18) SEQ ID NOs: 16 and 41, (19) SEQ ID NOs: 31 and 2, (20) SEQ ID NOs: 31 and 17, (21) SEQ ID NOs: 31 and 35, (22) SEQ ID NOs: 31 and 36, (23) SEQ ID NOs: 31 and 37, (24) SEQ ID NOs: 31 and 38, (25) SEQ ID NOs: 31 and 39, (26) SEQ ID NOs: 31 and 40, (27) SEQ ID NOs: 31 and 41, (28) SEQ ID NOs: 32 and 2, (29) SEQ ID NOs: 32 and 17, (30) SEQ ID NOs: 32 and 35, (31) SEQ ID NOs: 32 and 36, (32) SEQ ID NOs: 32 and 37, (33) SEQ ID NOs: 32 and 38, (34) SEQ ID NOs: 32 and 39, (35) SEQ ID NOs: 32 and 40, (36) SEQ ID NOs: 32 and 41, (37) SEQ ID NOs: 33 and 2, (38) SEQ ID NOs: 33 and 17, (39) SEQ ID NOs: 33 and 35, (40) SEQ ID NOs: 33 and 36, (41) SEQ ID NOs: 33 and 37, (42) SEQ ID NOs: 33 and 38, (43) SEQ ID NOs: 33 and 39, (44) SEQ ID NOs: 33 and 40, (45) SEQ ID NOs: 33 and 41, (46) SEQ ID NOs: 34 and 2, (47) SEQ ID NOs: 34 and 17, (48) SEQ ID NOs: 34 and 35, (49) SEQ ID NOs: 34 and 36, (50) SEQ ID NOs: 34 and 37, (51) SEQ ID NOs: 34 and 38, (52) SEQ ID NOs: 34 and 39, (53) SEQ ID NOs: 34 and 40, or (54) SEQ ID NOs: 34 and 41.

In other embodiments, both of the forward and reverse primers hybridize with the nucleic acid of the same microorganism species. In this regard, both of the first and second nucleic acids of the collection may hybridize with the nucleic acid of *Alicyclobacillus acidoterrestris*. In an embodiment, the collection may comprise an *Alicyclobacillus acidoterrestris*-specific collection comprising (1) SEQ ID NOs: 4 and 5, (2) SEQ ID NOs: 4 and 20, (3) SEQ ID NOs: 4 and 46, (4) SEQ ID NOs: 4 and 47, (5) SEQ ID NOs: 4 and 48, (6) SEQ ID NOs: 4 and 49, (7) SEQ ID NOs: 4 and 50, (8) SEQ ID NOs: 4 and 51, (9) SEQ ID NOs: 4 and 52, (10) SEQ ID NOs: 19 and 5, (11) SEQ ID NOs: 19 and 20, (12) SEQ ID NOs: 19 and 46, (13) SEQ ID NOs: 19 and 47, (14) SEQ ID NOs: 19 and 48, (15) SEQ ID NOs: 19 and 49, (16) SEQ ID NOs: 19 and 50, (17) SEQ ID NOs: 19 and 51, (18) SEQ ID NOs: 19 and 52, (19) SEQ ID NOs: 42 and 5, (20) SEQ ID NOs: 42 and 20, (21) SEQ ID NOs: 42 and 46, (22) SEQ ID NOs: 42 and 47, (23) SEQ ID NOs: 42 and 48, (24) SEQ ID NOs: 42 and 49, (25) SEQ ID NOs: 42 and 50, (26) SEQ ID NOs: 42 and 51, (27) SEQ ID NOs: 42 and 52, (28) SEQ ID NOs: 43 and 5, (29) SEQ ID NOs: 43 and 20, (30) SEQ ID NOs: 43 and 46, (31) SEQ ID NOs: 43 and 47, (32) SEQ ID NOs: 43 and 48, (33) SEQ ID NOs: 43 and 49, (34) SEQ ID NOs: 43 and 50, (35) SEQ ID NOs: 43 and 51, (36) SEQ ID NOs: 43 and 52, (37) SEQ ID NOs: 44 and 5, (38) SEQ ID NOs: 44 and 20, (39) SEQ ID NOs: 44 and 46, (40) SEQ ID NOs: 44 and 47, (41) SEQ ID NOs: 44 and 48, (42) SEQ ID NOs: 44 and 49, (43) SEQ ID NOs: 44 and 50, (44) SEQ ID NOs: 44 and 51, (45) SEQ ID NOs: 44 and 52, (46) SEQ ID NOs: 45 and 5, (47) SEQ ID NOs: 45 and 20, (48) SEQ ID NOs: 45 and 46, (49) SEQ ID NOs: 45 and 47, (50) SEQ ID NOs: 45 and 48, (51) SEQ ID NOs: 45 and 49, (52) SEQ ID NOs: 45 and 50, (53) SEQ ID NOs: 45 and 51, or (54) SEQ ID NOs: 45 and 52.

In another embodiment, both of the first and second nucleic acids of the collection may hybridize with *Alicyclobacillus acidiphilus*. In this regard, the collection may comprise (1) SEQ ID NOs: 7 and 8, (2) SEQ ID NOs: 7 and 23, (3) SEQ ID NOs: 7 and 58, (4) SEQ ID NOs: 7 and 59, (5) SEQ ID NOs: 7 and 60, (6) SEQ ID NOs: 7 and 61, (7) SEQ ID NOs: 7 and 62, (8) SEQ ID NOs: 7 and 63, (9) SEQ ID NOs: 7 and 64, (10) SEQ ID NOs: 7 and 65, (11) SEQ ID NOs: 7 and 66, (12) SEQ ID NOs: 22 and 8, (13) SEQ ID NOs: 22 and 23, (14) SEQ ID NOs: 22 and 58, (15) SEQ ID NOs: 22 and 59, (16) SEQ ID NOs: 22 and 60, (17) SEQ ID NOs: 22 and 61, (18) SEQ ID NOs: 22 and 62, (19) SEQ ID NOs: 22 and 63, (20) SEQ ID NOs: 22 and 64, (21) SEQ ID NOs: 22 and 65, (22) SEQ ID NOs: 22 and 66, (23) SEQ ID NOs: 53 and 8, (24) SEQ ID NOs: 53 and 23, (25) SEQ ID NOs: 53 and 58, (26) SEQ ID NOs: 53 and 59, (27) SEQ ID NOs: 53 and 60, (28) SEQ ID NOs: 53 and 61, (29) SEQ ID NOs: 53 and 62, (30) SEQ ID NOs: 53 and 63, (31) SEQ ID NOs: 53 and 64, (32) SEQ ID NOs: 53 and 65, (33) SEQ ID NOs: 53 and 66, (34) SEQ ID NOs: 54 and 8, (35) SEQ ID NOs: 54 and 23, (36) SEQ ID NOs: 54 and 58, (37) SEQ ID NOs: 54 and 59, (38) SEQ ID NOs: 54 and 60, (39) SEQ ID NOs: 54 and 61, (40) SEQ ID NOs: 54 and 62, (41) SEQ ID NOs: 54 and 63, (42) SEQ ID NOs: 54 and 64, (43) SEQ ID NOs: 54 and 65, (44) SEQ ID NOs: 54 and 66, (45) SEQ ID NOs: 55 and 8, (46) SEQ ID NOs: 55 and 23, (47) SEQ ID NOs: 55 and 58, (48) SEQ ID NOs: 55 and 59, (49) SEQ ID NOs: 55 and 60, (50) SEQ ID NOs: 55 and 61, (51) SEQ ID NOs: 55 and 62, (52) SEQ ID NOs: 55 and 63, (53) SEQ ID NOs: 55 and 64, (54) SEQ ID NOs: 55 and 65, (55) SEQ ID NOs: 55 and 66, (56) SEQ ID NOs: 56 and 8, (57) SEQ ID NOs: 56 and 23, (58) SEQ ID NOs: 56 and 58, (59) SEQ ID NOs: 56 and 59, (60) SEQ ID NOs: 56 and 60, (61) SEQ ID NOs: 56 and 61, (62) SEQ ID NOs: 56 and 62, (63) SEQ ID NOs: 56 and 63, (64) SEQ ID NOs: 56 and 64, (65) SEQ ID NOs: 56 and 65, (66) SEQ ID NOs: 56 and 66, (67) SEQ ID NOs: 57 and 8, (68) SEQ ID NOs: 57 and 23, (69) SEQ ID NOs: 57 and 58, (70) SEQ ID NOs: 57 and 59, (71) SEQ ID NOs: 57 and 60, (72) SEQ ID NOs: 57 and 61, (73) SEQ ID NOs: 57 and 62, (74) SEQ ID NOs: 57 and 63, (75) SEQ ID NOs: 57 and 64, (76) SEQ ID NOs: 57 and 65, or (77) SEQ ID NOs: 57 and 66.

In another embodiment, both of the first and second nucleic acids of the collection may hybridize with *Alicyclobacillus cycloheptanicus*. In this regard, the collection may comprise (1) SEQ ID NOs: 10 and 11, (2) SEQ ID NOs: 10 and 26, (3) SEQ ID NOs: 10 and 68, (4) SEQ ID NOs: 10 and 69, (5) SEQ ID NOs: 10 and 70, (6) SEQ ID NOs: 25 and 11, (7) SEQ ID NOs: 25 and 26, (8) SEQ ID NOs: 25 and 68, (9) SEQ ID NOs: 25 and 69, (10) SEQ ID NOs: 25 and 70, (11) SEQ ID NOs: 67 and 11, (12) SEQ ID NOs: 67 and 26, (13) SEQ ID NOs: 67 and 68, (14) SEQ ID NOs: 67 and 69, or (15) SEQ ID NOs: 67 and 70.

In another embodiment, both of the first and second nucleic acids of the collection may hybridize with *Alicyclobacillus herbarius*. In this regard, the collection may comprise (1) SEQ ID NOs: 13 and 14, (2) SEQ ID NOs: 13 and 29, (3) SEQ ID NOs: 13 and 73, (4) SEQ ID NOs: 13 and 74, (5) SEQ ID NOs: 28 and 14, (6) SEQ ID NOs: 28 and 29, (7) SEQ ID NOs: 28 and 73, (8) SEQ ID NOs: 28 and 74, (9) SEQ ID NOs: 71 and 14, (10) SEQ ID NOs: 71 and 29, (11) SEQ ID NOs: 71 and 73, (12) SEQ ID NOs: 71 and 74, (13) SEQ ID NOs: 72 and 14, (14) SEQ ID NOs: 72 and 29, (15) SEQ ID NOs: 72 and 73, or (16) SEQ ID NOs: 72 and 74.

In an embodiment of the invention, the collection of nucleic acids may include at least one primer and a probe, preferably at least one forward primer, at least one reverse primer, and at least one probe. The probe may comprise any of the nucleic acids described herein with respect to other aspects of the invention. In this regard, the collection may comprise (a) a first nucleic acid selected from the group consisting of SEQ ID NOs: 1, 4, 7, 10, 13, 16, 19, 22, 25, 28, 31-34, 42-45, 53-57, 67, and 71-72; (b) a second nucleic acid selected from the group consisting of SEQ ID NOs: 2, 5, 8, 11, 14, 17, 20, 23, 26, 29, 35-41, 46-52, 58-66, 68-70, and 73-74; and (c) a third nucleic acid selected from the group consisting of SEQ ID NOs: 3, 6, 9, 12, 15, 18, 21, 24, 27, and 30, wherein each of the nucleic acids has a length of no more than 35 nucleotides.

In an embodiment of the invention, the first, second, and third nucleic acids of the collection are all genus-specific nucleic acids. In this regard, each of the first, second, and third nucleic acids of the collection may hybridize with the nucleic acid of two or more *Alicyclobacillus* species. In an embodiment, the collection may comprise SEQ ID NOs: 3 or 18 in combination with any of the genus-specific collections (1)-(54) described herein. In an embodiment, the collection may comprise a genus-specific collection comprising (1) SEQ ID NOs: 1-3, (2) SEQ ID NOs: 1, 3 and 17, (3) SEQ ID NOs: 1, 3 and 35, (4) SEQ ID NOs: 1, 3 and 36, (5) SEQ ID NOs: 1, 3 and 37, (6) SEQ ID NOs: 1, 3 and 38, (7) SEQ ID NOs: 1, 3 and 39, (8) SEQ ID NOs: 1, 3 and 40, (9) SEQ ID NOs: 1, 3 and 41, (10) SEQ ID NOs: 16, 3 and 2, (11) SEQ ID NOs: 16, 3 and 17, (12) SEQ ID NOs: 16, 3 and 35, (13) SEQ ID NOs: 16, 3 and 36, (14) SEQ ID NOs: 16, 3 and 37, (15) SEQ ID NOs: 16, 3 and 38, (16) SEQ ID NOs: 16, 3 and 39, (17) SEQ ID NOs: 16, 3 and 40, (18) SEQ ID NOs: 16, 3 and 41, (19) SEQ ID NOs: 31, 3 and 2, (20) SEQ ID NOs: 31, 3 and 17, (21) SEQ ID NOs: 31, 3 and 35, (22) SEQ ID NOs: 31, 3 and 36, (23) SEQ ID NOs: 31, 3 and 37, (24) SEQ ID NOs: 31, 3 and 38, (25) SEQ ID NOs: 31, 3 and 39, (26) SEQ ID NOs: 31, 3 and 40, (27) SEQ ID NOs: 31, 3 and 41, (28) SEQ ID NOs: 32, 3 and 2, (29) SEQ ID NOs: 32, 3 and 17, (30) SEQ ID NOs: 32, 3 and 35, (31) SEQ ID NOs: 32, 3 and 36, (32) SEQ ID NOs: 32, 3 and 37, (33) SEQ ID NOs: 32, 3 and 38, (34) SEQ ID NOs: 32, 3 and 39, (35) SEQ ID NOs: 32, 3 and 40, (36) SEQ ID NOs: 32, 3 and 41, (37) SEQ ID NOs: 33, 3 and 2, (38) SEQ ID NOs: 33, 3 and 17, (39) SEQ ID NOs: 33, 3 and 35, (40) SEQ ID NOs: 33, 3 and 36, (41) SEQ ID NOs: 33, 3 and 37, (42) SEQ ID NOs: 33, 3 and 38, (43) SEQ ID NOs: 33, 3 and 39, (44) SEQ ID NOs: 33, 3 and 40, (45) SEQ ID NOs: 33, 3 and 41, (46) SEQ ID NOs: 34, 3 and 2, (47) SEQ ID NOs: 34, 3 and 17, (48) SEQ ID NOs: 34, 3 and 35, (49) SEQ ID NOs: 34, 3 and 36, (50) SEQ ID NOs: 34, 3 and 37, (51) SEQ ID NOs: 34, 3 and 38, (52) SEQ ID NOs: 34, 3 and 39, (53) SEQ ID NOs: 34, 3 and 40, (54) SEQ ID NOs: 34, 3 and 41, (55) SEQ ID NOs: 1, 2, and 18, (56) SEQ ID NOs: 1, 18 and 17, (57) SEQ ID NOs: 1, 18 and 35, (58) SEQ ID NOs: 1, 18 and 36, (59) SEQ ID NOs: 1, 18 and 37, (60) SEQ ID NOs: 1, 18 and 38, (61) SEQ ID NOs: 1, 18 and 39, (62) SEQ ID NOs: 1, 18 and 40, (63) SEQ ID NOs: 1, 18 and 41, (64) SEQ ID NOs: 16, 18 and 2, (65) SEQ ID NOs: 16, 18 and 17, (66) SEQ ID NOs: 16, 18 and 35, (67) SEQ ID NOs: 16, 18 and 36, (68) SEQ ID NOs: 16, 18 and 37, (69) SEQ ID NOs: 16, 18 and 38, (70) SEQ ID NOs: 16, 18 and 39, (71) SEQ ID NOs: 16, 18 and 40, (72) SEQ ID NOs: 16, 18 and 41, (73) SEQ ID NOs: 31, 18 and 2, (74) SEQ ID NOs: 31, 18 and 17, (75) SEQ ID NOs: 31, 18 and 35, (76) SEQ ID NOs: 31, 18 and 36, (77) SEQ ID NOs: 31, 18 and 37, (78) SEQ ID NOs: 31, 18 and 38, (79) SEQ ID NOs: 31, 18 and 39, (80) SEQ ID NOs: 31, 18 and 40, (81) SEQ ID NOs: 31, 18 and 41, (82) SEQ ID NOs: 32, 18 and 2, (83) SEQ ID NOs: 32, 18 and 17, (84) SEQ ID NOs: 32, 18 and 35, (85) SEQ ID NOs: 32, 18 and 36, (86) SEQ ID NOs: 32, 18 and 37, (87) SEQ ID NOs: 32, 18 and 38, (88) SEQ ID NOs: 32, 18 and 39, (89) SEQ ID NOs: 32, 18 and 40, (90) SEQ ID NOs: 32, 18 and 41, (91) SEQ ID NOs: 33, 18 and 2, (92) SEQ ID NOs: 33, 18 and 17, (93) SEQ ID NOs: 33, 18 and 35, (94) SEQ ID NOs: 33, 18 and 36, (95) SEQ ID NOs: 33, 18 and 37, (96) SEQ ID NOs: 33, 18 and 38, (97) SEQ ID NOs: 33, 18 and 39, (98) SEQ ID NOs: 33, 18 and 40, (99) SEQ ID NOs: 33, 18 and 41, (100) SEQ ID NOs: 34, 18 and 2, (101) SEQ ID NOs: 34, 18 and 17, (102) SEQ ID NOs: 34, 18 and 35, (103) SEQ ID NOs: 34, 18 and 36, (104) SEQ ID NOs: 34, 18 and 37, (105) SEQ ID NOs: 34, 18 and 38, (106) SEQ ID NOs: 34, 18 and 39, (107) SEQ ID NOs: 34, 18 and 40, or (108) SEQ ID NOs: 34, 18 and 41.

In an embodiment of the invention, the first, second, and third nucleic acids of the collection are all *Alicyclobacillus acidoterrestris*-specific nucleic acids. In this regard, each of the first, second, and third nucleic acids of the collection may hybridize with the nucleic acid of *Alicyclobacillus acidoterrestris*. In an embodiment, the collection may comprise SEQ ID NO: 6 or 21 in combination with any of the *Alicyclobacillus acidoterrestris*-specific collections (1)-(54) described herein. In an embodiment, the collection may comprise an *Alicyclobacillus acidoterrestris*-specific collection comprising (1) SEQ ID NOs: 4-6, (2) SEQ ID NOs: 4, 6 and 20, (3) SEQ ID NOs: 4, 6 and 46, (4) SEQ ID NOs: 4, 6 and 47, (5) SEQ ID NOs: 4, 6 and 48, (6) SEQ ID NOs: 4, 6 and 49, (7) SEQ ID NOs: 4, 6 and 50, (8) SEQ ID NOs: 4, 6 and 51, (9) SEQ ID NOs: 4, 6 and 52, (10) SEQ ID NOs: 19, 6 and 5, (11) SEQ ID NOs: 19, 6 and 20, (12) SEQ ID NOs: 19, 6 and 46, (13) SEQ ID NOs: 19, 6 and 47, (14) SEQ ID NOs: 19, 6 and 48, (15) SEQ ID NOs: 19, 6 and 49, (16) SEQ ID NOs: 19, 6 and 50, (17) SEQ ID NOs: 19, 6 and 51, (18) SEQ ID NOs: 19, 6 and 52, (19) SEQ ID NOs: 42, 6 and 5, (20) SEQ ID NOs: 42, 6 and 20, (21) SEQ ID NOs: 42, 6 and 46, (22) SEQ ID NOs: 42, 6 and 47, (23) SEQ ID NOs: 42, 6 and 48, (24) SEQ ID NOs: 42, 6 and 49, (25) SEQ ID NOs: 42, 6 and 50, (26) SEQ ID NOs: 42, 6 and 51, (27) SEQ ID NOs: 42, 6 and 52, (28) SEQ ID NOs: 43, 6 and 5, (29) SEQ ID NOs: 43, 6 and 20, (30) SEQ ID NOs: 43, 6 and 46, (31) SEQ ID NOs: 43, 6 and 47, (32) SEQ ID NOs: 43, 6 and 48, (33) SEQ ID NOs: 43, 6 and 49, (34) SEQ ID NOs: 43, 6 and 50, (35) SEQ ID NOs: 43, 6 and 51, (36) SEQ ID NOs: 43, 6 and 52, (37) SEQ ID NOs: 44, 6 and 5, (38) SEQ ID NOs: 44, 6 and 20, (39) SEQ ID NOs: 44, 6 and 46, (40) SEQ ID NOs: 44, 6 and 47, (41) SEQ ID NOs: 44, 6 and 48, (42) SEQ ID NOs: 44, 6 and 49, (43) SEQ ID NOs: 44, 6 and 50, (44) SEQ ID NOs: 44, 6 and 51, (45) SEQ ID NOs: 44, 6 and 52, (46) SEQ ID NOs: 45, 6 and 5, (47) SEQ ID NOs: 45, 6 and 20, (48) SEQ ID NOs: 45, 6 and 46, (49) SEQ ID NOs: 45, 6 and 47, (50) SEQ ID NOs: 45, 6 and 48, (51) SEQ ID NOs: 45, 6 and 49, (52) SEQ ID NOs: 45, 6 and 50, (53) SEQ ID NOs: 45, 6 and 51, (54) SEQ ID NOs: 45, 6 and 52, (55) SEQ ID NOs: 4-6, (56) SEQ ID NOs: 4, 21 and 20, (57) SEQ ID NOs: 4, 21 and 46, (58) SEQ ID NOs: 4, 21 and 47, (59) SEQ ID NOs: 4, 21 and 48, (60) SEQ ID NOs: 4, 21 and 49, (61) SEQ ID NOs: 4, 21 and 50, (62) SEQ ID NOs: 4, 21 and 51, (63) SEQ ID NOs: 4, 21 and 52, (64) SEQ ID NOs: 19, 21 and 5, (65) SEQ ID NOs: 19, 21 and 20, (66) SEQ ID NOs: 19, 21 and 46, (67) SEQ ID NOs: 19, 21 and 47, (68) SEQ ID NOs: 19, 21 and 48, (69) SEQ ID NOs: 19, 21 and 49, (70) SEQ ID NOs: 19, 21 and 50, (71) SEQ ID NOs: 19, 21 and 51, (72) SEQ ID NOs: 19, 21 and 52, (73) SEQ ID NOs: 42, 21 and 5, (74) SEQ ID NOs: 42, 21 and 20, (75) SEQ ID NOs: 42, 21 and 46, (76) SEQ ID NOs: 42, 21 and 47, (77) SEQ ID NOs: 42, 21 and 48, (78) SEQ ID NOs: 42, 21 and 49, (79) SEQ ID NOs: 42, 21 and 50, (80) SEQ ID NOs: 42, 21 and 51, (81) SEQ ID NOs: 42, 21 and 52, (82) SEQ ID NOs: 43, 21 and 5, (83) SEQ ID NOs: 43, 21 and 20, (84) SEQ ID NOs: 43, 21 and 46, (85) SEQ ID NOs: 43, 21 and 47, (86) SEQ ID NOs: 43, 21 and 48, (87) SEQ ID NOs: 43, 21 and 49, (88) SEQ ID NOs: 43, 21 and 50, (89) SEQ ID NOs: 43, 21 and 51, (90) SEQ ID NOs: 43, 21 and 52, (91) SEQ ID NOs: 44, 21 and 5, (92) SEQ ID NOs: 44, 21 and 20, (93) SEQ ID NOs: 44, 21 and 46, (94) SEQ ID NOs: 44, 21 and 47, (95) SEQ ID NOs: 44, 21 and 48, (96) SEQ ID NOs: 44, 21 and 49, (97) SEQ ID NOs: 44, 21 and 50, (98) SEQ ID NOs: 44, 21 and 51, (99) SEQ ID NOs: 44, 21 and 52, (100) SEQ ID NOs: 45, 21 and 5, (101) SEQ ID NOs: 45, 21 and 20, (102) SEQ ID NOs: 45, 21 and 46, (103) SEQ ID NOs: 45, 21 and 47, (104) SEQ ID NOs: 45, 21 and 48, (105) SEQ ID NOs: 45, 21 and 49, (106) SEQ ID NOs: 45, 21 and 50, (107) SEQ ID NOs: 45, 21 and 51, or (108) SEQ ID NOs: 45, 21 and 52.

In an embodiment of the invention, the first, second, and third nucleic acids of the collection are all *Alicyclobacillus acidiphilus*-specific nucleic acids. In this regard, each of the first, second, and third nucleic acids of the collection may hybridize with the nucleic acid of *Alicyclobacillus acidiphilus*. In an embodiment, the collection may comprise SEQ ID NOs: 9 or 24 in combination with any of the *Alicyclobacillus acidiphilus*-specific collections (1)-(77) described herein. In an embodiment, the collection may comprise an *Alicyclobacillus acidiphilus*-specific collection comprising (1) SEQ ID NOs: 7-9, (2) SEQ ID NOs: 7, 9 and 23, (3) SEQ ID NOs: 7, 9 and 58, (4) SEQ ID NOs: 7, 9 and 59, (5) SEQ ID NOs: 7, 9 and 60, (6) SEQ ID NOs: 7, 9 and 61, (7) SEQ ID NOs: 7, 9 and 62, (8) SEQ ID NOs: 7, 9 and 63, (9) SEQ ID NOs: 7, 9 and 64, (10) SEQ ID NOs: 7, 9 and 65, (11) SEQ ID NOs: 7, 9 and 66, (12) SEQ ID NOs: 22, 9 and 8, (13) SEQ ID NOs: 22, 9 and 23, (14) SEQ ID NOs: 22, 9 and 58, (15) SEQ ID NOs: 22, 9 and 59, (16) SEQ ID NOs: 22, 9 and 60, (17) SEQ ID NOs: 22, 9 and 61, (18) SEQ ID NOs: 22, 9 and 62, (19) SEQ ID NOs: 22, 9 and 63, (20) SEQ ID NOs: 22, 9 and 64, (21) SEQ ID NOs: 22, 9 and 65, (22) SEQ ID NOs: 22, 9 and 66, (23) SEQ ID NOs: 53, 9 and 8, (24) SEQ ID NOs: 53, 9 and 23, (25) SEQ ID NOs: 53, 9 and 58, (26) SEQ ID NOs: 53, 9 and 59, (27) SEQ ID NOs: 53, 9 and 60, (28) SEQ ID NOs: 53, 9 and 61, (29) SEQ ID NOs: 53, 9 and 62, (30) SEQ ID NOs: 53, 9 and 63, (31) SEQ ID NOs: 53, 9 and 64, (32) SEQ ID NOs: 53, 9 and 65, (33) SEQ ID NOs: 53, 9 and 66, (34) SEQ ID NOs: 54, 9 and 8, (35) SEQ ID NOs: 54, 9 and 23, (36) SEQ ID NOs: 54, 9 and 58, (37) SEQ ID NOs: 54, 9 and 59, (38) SEQ ID NOs: 54, 9 and 60, (39) SEQ ID NOs: 54, 9 and 61, (40) SEQ ID NOs: 54, 9 and 62, (41) SEQ ID NOs: 54, 9 and 63, (42) SEQ ID NOs: 54, 9 and 64, (43) SEQ ID NOs: 54, 9 and 65, (44) SEQ ID NOs: 54, 9 and 66, (45) SEQ ID NOs: 55, 9 and 8, (46) SEQ ID NOs: 55, 9 and 23, (47) SEQ ID NOs: 55, 9 and 58, (48) SEQ ID NOs: 55, 9 and 59, (49) SEQ ID NOs: 55, 9 and 60, (50), SEQ ID NOs: 55, 9 and 61, (51) SEQ ID NOs: 55, 9 and 62, (52) SEQ ID NOs: 55, 9 and 63, (53) SEQ ID NOs: 55, 9 and 64, (54) SEQ ID NOs: 55, 9 and 65, (55) SEQ ID NOs: 55, 9 and 66, (56) SEQ ID NOs: 56, 9 and 8, (57) SEQ ID NOs: 56, 9 and 23, (58) SEQ ID NOs: 56, 9 and 58, (59) SEQ ID NOs: 56, 9 and 59, (60) SEQ ID NOs: 56, 9 and 60, (61) SEQ ID NOs: 56, 9 and 61, (62) SEQ ID NOs: 56, 9 and 62, (63) SEQ ID NOs: 56, 9 and 63, (64) SEQ ID NOs: 56, 9 and 64, (65) SEQ ID NOs: 56, 9 and 65, (66) SEQ ID NOs: 56, 9 and 66, (67) SEQ ID NOs: 57, 9 and 8, (68) SEQ ID NOs: 57, 9 and 23, (69) SEQ ID NOs: 57, 9 and 58, (70) SEQ ID NOs: 57, 9 and 59, (71) SEQ ID NOs: 57, 9 and 60, (72) SEQ ID NOs: 57, 9 and 61, (73) SEQ ID NOs: 57, 9 and 62, (74) SEQ ID NOs: 57, 9 and 63, (75) SEQ ID NOs: 57, 9 and 64, (76) SEQ ID NOs: 57, 9 and 65, (77) SEQ ID NOs: 57, 9 and 66, (78) SEQ ID NOs: 7, 8, and 24, (79) SEQ ID NOs: 7, 24 and 23, (80) SEQ ID NOs: 7, 24 and 58, (81) SEQ ID NOs: 7, 24 and 59, (82) SEQ ID NOs: 7, 24 and 60, (83) SEQ ID NOs: 7, 24 and 61, (84) SEQ ID NOs: 7, 24 and 62, (85) SEQ ID NOs: 7, 24 and 63, (86) SEQ ID NOs: 7, 24 and 64, (87) SEQ ID NOs: 7, 24 and 65, (88) SEQ ID NOs: 7, 24 and 66, (89) SEQ ID NOs: 22, 24 and 8, (90) SEQ ID NOs: 22, 24 and 23, (91) SEQ ID NOs: 22, 24 and 58, (92) SEQ ID NOs: 22, 24 and 59, (93) SEQ ID NOs: 22, 24 and 60, (94) SEQ ID NOs: 22, 24 and 61, (95) SEQ ID NOs: 22, 24 and 62, (96) SEQ ID NOs: 22, 24 and 63, (97) SEQ ID NOs: 22, 24 and 64, (98) SEQ ID NOs: 22, 24 and 65, (99) SEQ ID NOs: 22, 24 and 66, (100) SEQ ID NOs: 53, 24 and 8, (101) SEQ ID NOs: 53, 24 and 23, (102) SEQ ID NOs: 53, 24 and 58, (103) SEQ ID NOs: 53, 24 and 59, (104) SEQ ID NOs: 53, 24 and 60, (105) SEQ ID NOs: 53, 24 and 61, (106) SEQ ID NOs: 53, 24 and 62, (107) SEQ ID NOs: 53, 24 and 63, (108) SEQ ID NOs: 53, 24 and 64, (109) SEQ ID NOs: 53, 24 and 65, (110) SEQ ID NOs: 53, 24 and 66, (111) SEQ ID NOs: 54, 24 and 8, (112) SEQ ID NOs: 54, 24 and 23, (113) SEQ ID NOs: 54, 24 and 58, (114) SEQ ID NOs: 54, 24 and 59, (115) SEQ ID NOs: 54, 24 and 60, (116) SEQ ID NOs: 54, 24 and 61, (117) SEQ ID NOs: 54, 24 and 62, (118) SEQ ID NOs: 54, 24 and 63, (119) SEQ ID NOs: 54, 24 and 64, (120) SEQ ID NOs: 54, 24 and 65, (121) SEQ ID NOs: 54, 24 and 66, (122) SEQ ID NOs: 55, 24 and 8, (123) SEQ ID NOs: 55, 24 and 23, (124) SEQ ID NOs: 55, 24 and 58, (125) SEQ ID NOs: 55, 24 and 59, (126) SEQ ID NOs: 55, 24 and 60, (127) SEQ ID NOs: 55, 24 and 61, (128) SEQ ID NOs: 55, 24 and 62, (129) SEQ ID NOs: 55, 24 and 63, (130) SEQ ID NOs: 55, 24 and 64, (131) SEQ ID NOs: 55, 24 and 65, (132) SEQ ID NOs: 55, 24 and 66, (133) SEQ ID NOs: 56, 24 and 8, (134) SEQ ID NOs: 56, 24 and 23, (135) SEQ ID NOs: 56, 24 and 58, (136) SEQ ID NOs: 56, 24 and 59, (137) SEQ ID NOs: 56, 24 and 60, (138) SEQ ID NOs: 56, 24 and 61, (139) SEQ ID NOs: 56, 24 and 62, (140) SEQ ID NOs: 56, 24 and 63, (141) SEQ ID NOs: 56, 24 and 64, (142) SEQ ID NOs: 56, 24 and 65, (143) SEQ ID NOs: 56, 24 and 66, (144) SEQ ID NOs: 57, 24 and 8, (145) SEQ ID NOs: 57, 24 and 23, (146) SEQ ID NOs: 57, 24 and 58, (147) SEQ ID NOs: 57, 24 and 59, (148) SEQ ID NOs: 57, 24 and 60, (149) SEQ ID NOs: 57, 24 and 61, (150) SEQ ID NOs: 57, 24 and 62, (151) SEQ ID NOs: 57, 24 and 63, (152) SEQ ID NOs: 57, 24 and 64, (153) SEQ ID NOs: 57, 24 and 65, or (154) SEQ ID NOs: 57, 24 and 66.

In an embodiment of the invention, the first, second, and third nucleic acids of the collection are all *Alicyclobacillus cycloheptanicus*-specific nucleic acids. In this regard, each of the first, second, and third nucleic acids of the collection may hybridize with the nucleic acid of *Alicyclobacillus cycloheptanicus*. In an embodiment, the collection may comprise SEQ ID NO: 12 or 27 in combination with any of the *Alicyclobacillus cycloheptanicus*-specific collections (1)-(15) described herein. In an embodiment, the collection may comprise an *Alicyclobacillus cycloheptanicus*-specific collection comprising (1) SEQ ID NOs: 10-12, (2) SEQ ID NOs: 10, 12 and 26, (3) SEQ ID NOs: 10, 12 and 68, (4) SEQ ID NOs: 10, 12 and 69, (5) SEQ ID NOs: 10, 12 and 70, (6) SEQ ID NOs: 25, 12 and 11, (7) SEQ ID NOs: 25, 12 and 26, (8) SEQ ID NOs: 25, 12 and 68, (9) SEQ ID NOs: 25, 12 and 69, (10) SEQ ID NOs: 25, 12 and 70, (11) SEQ ID NOs: 67, 12 and 11, (12) SEQ ID NOs: 67, 12 and 26, (13) SEQ ID NOs: 67, 12 and 68, (14) SEQ ID NOs: 67, 12 and 69, (15) SEQ ID NOs: 67, 12 and 70, (16) SEQ ID NOs: 10, 11, and 27, (17) SEQ ID NOs: 10, 27 and 26, (18) SEQ ID NOs: 10, 27 and 68, (19) SEQ ID NOs: 10, 27 and 69, (20) SEQ ID NOs: 10, 27 and 70, (21) SEQ ID NOs: 25, 27 and 11, (22) SEQ ID NOs: 25, 27 and 26, (23) SEQ ID NOs: 25, 27 and 68, (24) SEQ ID NOs: 25, 27 and 69, (25) SEQ ID NOs: 25, 27 and 70, (26) SEQ ID NOs: 67, 27 and 11, (27) SEQ ID NOs: 67, 27 and 26, (28) SEQ ID NOs: 67, 27 and 68, (29) SEQ ID NOs: 67, 27 and 69, or (30) SEQ ID NOs: 67, 27 and 70.

In an embodiment of the invention, the first, second, and third nucleic acids of the collection are all *Alicyclobacillus herbarius*-specific nucleic acids. In this regard, each of the first, second, and third nucleic acids of the collection may hybridize with the nucleic acid of *Alicyclobacillus herbarius*. In an embodiment, the collection may comprise SEQ ID NO: 15 or 30 in combination with any of the *Alicyclobacillus herbarius*-specific collections (1)-(16) described herein. In an embodiment, the collection may comprise an *Alicyclobacillus herbarius*-specific collection comprising (1) SEQ ID NOs: 13-15, (2) SEQ ID NOs: 13, 15 and 29, (3) SEQ ID NOs: 13, 15 and 73, (4) SEQ ID NOs: 13, 15 and 74, (5) SEQ ID NOs: 28, 15 and 14, (6) SEQ ID NOs: 28, 15 and 29, (7) SEQ ID NOs: 28, 15 and 73, (8) SEQ ID NOs: 28, 15 and 74, (9) SEQ ID NOs: 71, 15 and 14, (10) SEQ ID NOs: 71, 15 and 29, (11) SEQ ID NOs: 71, 15 and 73, (12) SEQ ID NOs: 71, 15 and 74, (13) SEQ ID NOs: 72, 15 and 14, (14) SEQ ID NOs: 72, 15 and 29, (15) SEQ ID NOs: 72, 15 and 73, (16) SEQ ID NOs: 72, 15 and 74, (17) SEQ ID NOs: 13, 14, and 30, (18) SEQ ID NOs: 13, 30 and 29, (19) SEQ ID NOs: 13, 30 and 73, (20) SEQ ID NOs: 13, 30 and 74, (21) SEQ ID NOs: 28, 30 and 14, (22) SEQ ID NOs: 28, 30 and 29, (23) SEQ ID NOs: 28, 30 and 73, (24) SEQ ID NOs: 28, 30 and 74,

(25) SEQ ID NOs: 71, 30 and 14, (26) SEQ ID NOs: 71, 30 and 29, (27) SEQ ID NOs: 71, 30 and 73, (28) SEQ ID NOs: 71, 30 and 74, (29) SEQ ID NOs: 72, 30 and 14, (30) SEQ ID NOs: 72, 30 and 29, (31) SEQ ID NOs: 72, 30 and 73, or (32) SEQ ID NOs: 72, 30 and 74.

In an embodiment, the collection comprises two or more nucleic acids comprising (a) SEQ ID NOs: 1-3; (b) SEQ ID NOs: 4-6; (c) SEQ ID NOs: 7-9; (d) SEQ ID NOs: 10-12; or (e) SEQ ID NOs: 13-15, wherein each of the nucleic acids has a length of no more than 35 nucleotides. In another embodiment, the collection comprises two or more nucleic acids consisting of: (a) SEQ ID NOs: 16-18; (b) SEQ ID NOs: 19-21; (c) SEQ ID NOs: 22-24; (d) SEQ ID NOs: 25-27; or (e) SEQ ID NOs: 28-30. In an embodiment, the collection may include sequences that are complementary to any one or more of SEQ ID NOs: 1-74.

The collection of nucleic acids may comprise nucleic acids for the detection of any one, two, three, or four of the *Alicyclobacillus* species described herein either alone or in combination with any of the genus-specific nucleic acids described herein. In an embodiment of the invention, the collection of nucleic acids comprises nucleic acids for the detection of all four of the *Alicyclobacillus* species described herein in combination with any of the genus-specific nucleic acids described herein.

By "nucleotide sequence" or "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the inventive nucleic acid does not comprise any insertions, deletions, inversions, and/or substitutions. However, it may be suitable in some instances, as discussed herein, for the nucleic acid to comprise one or more insertions, deletions, inversions, and/or substitutions.

The inventive nucleic acids can be constructed based on chemical synthesis and/or enzymatic ligation reactions using procedures known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

An embodiment of the invention provides an assay kit comprising a collection of nucleic acids for the specific detection of one or more species of one or more microorganisms. The assay kit may comprise one or more collections of nucleic acids for the detection of any one, two, three, or four of the *Alicyclobacillus* species described herein either alone or in combination with any of the genus-specific collections described herein. In an embodiment of the invention, the assay kit comprises collections of nucleic acids for the detection of all four of the *Alicyclobacillus* species described herein in combination with any of the genus-specific collections described herein. In an embodiment of the invention, the assay kit may further comprise any one or more of DNA polymerase, buffer, deoxyribonucleotide triphosphates (dNTP), and Mg$^{++}$.

The DNA polymerase is not limited and may be any DNA polymerase suitable for qPCR or PCR. Exemplary DNA polymerases include *Thermus aquaticus* (Taq) polymerase and *Pyrococcus furiosus* (Pfu) polymerase.

The buffer is not limited and may be any buffer suitable for PCR or qPCR. Exemplary buffers include a combination of KCl, Tris and MgCl$_2$ and a combination of (NH4)$_2$SO$_4$, Tris-HCl, MgCl$_2$, β-Mercapthoethanol, and EDTA.

An embodiment of the invention provides a support comprising any of the inventive nucleic acids or collections of nucleic acids described herein immobilized on the support. Another embodiment of the invention provides a support comprising the sample to be tested immobilized on the support, and the one or more inventive nucleic acid or one or more collection of nucleic acids is applied to the support. The support may be any support suitable for immobilizing the inventive nucleic acids. Exemplary supports are described in U.S. Pat. No. 6,821,771, which is incorporated herein by reference in its entirety. Other exemplary supports include GENEDISC plates available from Pall Corporation, Port Washington, N.Y., USA.

The support may further comprise a detectable label. The label may be any label suitable for detecting a complex of the inventive nucleic acid with microorganism nucleic acid. Exemplary detectable labels may include any one or more of radioactive labels, non-radioactive labels, fluorescent labels, and chemiluminescent labels.

Still another embodiment of the invention provides a method of detecting the presence of one or more *Alicyclobacillus* microorganisms in a foodstuff, the method comprising: (a) obtaining at least one test sample comprising isolated microorganism nucleic acid from foodstuff; (b) contacting any of the inventive nucleic acids, collections of nucleic acids, or supports described herein with the at least one test sample under conditions allowing for a complex to form between the nucleic acid and the microorganism nucleic acid; (c) detecting the complex; and (d) comparing a presence of the complex in the at least one test sample with an absence of complex from a negative sample that lacks microorganism nucleic acid, wherein detection of the complex is indicative of the presence of one or more *Alicyclobacillus* microorganisms.

The method may comprise obtaining a sample of the foodstuff to be tested and culturing microorganisms in the sample in any suitable manner. For example, when the foodstuff is fruit juice, the sample may be any one or more of fruit juice concentrate, pasteurized fruit juice, unpasteurized fruit juice, other fruit juice, or any further additives or ingredients of fruit juice. Further additives and ingredients of fruit juice may include, for example, any one or more of water (e.g., condensation water and/or water added to the final juice product), soluble additives, and sweeteners such as, e.g., sugar (solid or liquid).

The method may comprise culturing the microorganisms in any suitable culturing medium as is known in the art. The culturing medium may be selected depending on the nature of the foodstuff and microorganism to be tested. Exemplary culturing media may include yeast-sucrose-glucose (YSG) media, potato dextrose media, and broth for *Alicyclobacillus* (BAT) media.

The microorganisms may be cultured at any suitable temperature and for any suitable duration as is known in the art. The culturing temperature and duration may be selected depending on the nature of the foodstuff and microorganism to be tested. For example, the microorganisms may be cultured at a temperature of about 40° C. to about 60° C., preferably from about 45° C. to about 50° C. The microorganisms may be cultured for about 1 day to about 14 days, preferably from about 2 days to about 7 days.

The method may comprise extracting nucleic acid from the microorganisms in any suitable manner as is known in the art. The nucleic acid may be RNA and/or DNA. The protocol for extracting nucleic acid may be selected depending on the nature of the foodstuff, microorganism, and nucleic acid to be tested as is known in the art. Preferably, the nucleic acid is extracted in any manner that lyses Gram positive and Gram negative bacteria and which recovers a testable amount of DNA without using polymerase chain reaction (PCR) inhibitors. The nucleic acid extraction may be carried out using any of a variety of commercially available nucleic acid extraction kits according to the manufacturer's instructions. Exemplary DNA extraction kits may include, for example, PFOOD kit (available from Pall Corporation, Port Washington, N.Y., USA).

The method comprises contacting the inventive nucleic acid, collection of nucleic acids, or support with the at least one test sample under conditions allowing for a complex to form between the inventive nucleic acid and the microorganism nucleic acid. In this regard, the method comprises contacting the sample of extracted nucleic acid with the inventive nucleic acid under conditions which allow the inventive nucleic acid to specifically hybridize with microorganism nucleic acid as is known in the art. The method may comprise amplifying the inventive nucleic acid and the microorganism nucleic acid using any suitable type of PCR as is known in the art.

The method comprises detecting the complex. The complex may be detected using, for example, a radioactive label or a dye as is known in the art. In a preferred embodiment, the method comprises measuring light emitted from a fluorescent dye using, e.g., a laser. Detecting the complex may, optionally, further comprise measuring the amount of complex formed.

The method may further comprise comparing a presence of the complex in the at least one test sample with an absence of complex from a negative sample that lacks microorganism nucleic acid. The presence of complex from the at least one test sample is indicative of the presence of one or more microorganisms and the absence of complex from the at least one test sample is indicative of the absence of one or more microorganisms. In an embodiment of the invention, the method comprises determining a background level of signal generated by the label in the negative sample that lacks microorganism nucleic acid and comparing the background level of signal with the level of signal detected in the test sample. A level of signal that is higher or lower in the test sample as compared to that measured in the negative sample may be indicative of the presence of one or more microorganisms.

In an embodiment, the method optionally comprises comparing an amount of complex in the at least one test sample with an amount of complex from a negative sample that lacks microorganism nucleic acid, wherein an increased amount of complex from the at least one test sample is indicative of the presence of one or more microorganisms. In this regard, the sample is negative for the foodstuff-spoiling microorganism if the amount of complex detected in the sample is no more than the amount of complex that is detected in a negative sample that is known to lack the microorganism nucleic acid. The sample is positive for the foodstuff-spoiling microorganism if the amount of complex detected in the sample is more than the amount of complex that is detected in a negative sample that is known to lack the microorganism nucleic acid.

The method may, advantageously, comprise testing for the presence of microorganisms in more than one different foodstuff sample simultaneously. In this regard, the at least one test sample may be two or more different samples tested sequentially or simultaneously, i.e., 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more samples sequentially or simultaneously.

The method may comprise detecting the presence of any one or more microorganisms that causes spoilage of foodstuff. In an embodiment of the invention, the method comprises detecting the presence of one or more microorganisms of the genus *Alicyclobacillus* that may or may not cause foodstuff spoilage in a sample of foodstuff. In this regard, the method may comprise detecting the presence of two or more of any of a variety of different species of microorganisms within the genus *Alicyclobacillus* using any of the genus-specific nucleic acids or collections thereof described herein.

In another embodiment, the method comprises detecting the presence of one or more species of microorganisms that cause spoilage in a sample of foodstuff. In this regard, the method may comprise detecting the presence of any two or more of a variety of different species of microorganisms within the genus *Alicyclobacillus* that cause spoilage in a sample of foodstuff using any of the species-specific nucleic acids or collections thereof described herein. The method may comprise detecting, for example, any one or more of *Alicyclobacillus acidoterrestris*, *Alicyclobacillus acidiphilus*, *Alicyclobacillus cycloheptanicus*, and *Alicyclobacillus herbarius*.

The method may comprise detecting microorganisms in any foodstuff. The foodstuff may be, for example, any one or more of dairy products; fats, oils, and fat emulsions; edible ices (including, e.g., sherbet and sorbet); fruits and vegetables (including, e.g., mushrooms and fungi, roots and tubers, pulses and legumes, and aloe vera); seaweeds; nuts and seeds; confectioneries; cereals and cereal products; baked goods (e.g., bread); meat and meat products (including, e.g., poultry and game); fish and fish products (including mollusks, crustaceans, and echinoderms); eggs and egg products; sweeteners, including, e.g., honey and sugar (solid or liquid); salts, spices, soups, sauces, salads, protein products; foodstuffs intended for particular nutritional uses; and beverages (e.g., water, fruit juice, beer, and wine). In a preferred embodiment, the foodstuff is fruit juice.

Another embodiment of the invention provides a method of detecting the presence of one or more *Alicyclobacillus* microorganisms in an environment, the method comprising: (a) obtaining at least one test sample comprising isolated microorganism nucleic acid from the environment; (b) contacting any of the inventive nucleic acids, collections of nucleic acids, or supports described herein with the at least one test sample under conditions allowing for a complex to form between the nucleic acid and the microorganism nucleic acid; (c) detecting the complex; and (d) comparing a presence of the complex in the at least one test sample with an absence of complex from a negative sample that lacks microorganism nucleic acid, wherein detection of the complex is indicative of the presence of one or more *Alicyclobacillus* microorganisms. In an embodiment of the invention, the environment is the environment in which manufacture, processing, and/or packaging (e.g., bottling) of foodstuff occurs. For example, the environmental sample may be an air sample or a sample from the surface of an object employed in the manufacture, processing, and/or packaging (e.g., bottling) of foodstuff. For example, the surface may be the surface of a bottle or can to be used to package a foodstuff. The method may otherwise be as described herein with respect to other aspects of the invention.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, 90% or can be 100%.

The following examples further illustrate the invention but, of course, should not be construed as in any way limiting its scope.

EXAMPLE 1

This example demonstrates the detection of microorganisms within the genus *Alicyclobacillus* generally (*Alicyclobacillus* spp.) as well as the species *Alicyclobacillus acidoterrestris*, *Alicyclobacillus acidiphilus*, *Alicyclobacillus cycloheptanicus*, and *Alicyclobacillus herbarius* using the inventive nucleic acids.

*Alicyclobacillus* species are obtained from American Type Culture Collection (ATCC) or Leibniz Institute DSMZ-German Collection of Microorganisms and Cell Cultures (DSM). Genomic DNA is isolated from *Alicyclobacillus acidocaldarius* (ATCC 43034), *Alicyclobacillus acidoterrestris* (DSM2498), *Alicyclobacillus acidiphilus* (DSM14558), *Alicyclobacillus cycloheptanicus* (ATCC49029), and *Alicyclobacillus herbarius* (DSM13609) using a DNA Extraction Kit (available from Pall Corporation, Port Washington, N.Y., USA) ("target DNA"). Bacterial DNA is diluted with 10 mM Tris-pH 8.3 to a concentration of 150,000 genomic units (GU)/μl. Tris-pH 8.3 buffer (10 mM) is used as a no target control (NTC).

A genus-specific (*Alicyclobacillus* spp.) collection of nucleic acids including a forward primer (SEQ ID NO: 16), a reverse primer (SEQ ID NO: 17), and a probe (SEQ ID NO: 18) is used to test DNA from *Alicyclobacillus acidocaldarius*. An *Alicyclobacillus acidoterrestris*-specific collection of nucleic acids including a forward primer (SEQ ID NO: 19), a reverse primer (SEQ ID NO: 20), and a probe (SEQ ID NO: 21) is used to test DNA from *Alicyclobacillus acidoterrestris*. An *Alicyclobacillus acidiphilus*-specific collection of nucleic acids including a forward primer (SEQ ID NO: 22), a reverse primer (SEQ ID NO: 23), and a probe (SEQ ID NO: 24) is used to test DNA from *Alicyclobacillus acidiphilus*. An *Alicyclobacillus cycloheptanicus*-specific collection of nucleic acids including a forward primer (SEQ ID NO: 25), a reverse primer (SEQ ID NO: 26), and a probe (SEQ ID NO: 27) is used to test DNA from *Alicyclobacillus cycloheptanicus*. An *Alicyclobacillus herbarius*-specific collection of nucleic acids including a forward primer (SEQ ID NO: 28), a reverse primer (SEQ ID NO: 29), and a probe (SEQ ID NO: 30) is used to test DNA from *Alicyclobacillus herbarius*. The DNA from each species is tested at 0 (no-target control (NTC)), 25 GU per PCR well, or 12.5 GU per PCR well. The probes are labeled with 6-FAM fluorescent dye at 5' and BHQ1 quencher at 3'.

A GENEDISC plate (available from Pall Corporation, Port Washington, N.Y., USA) is prepared according the manufacturer's instructions.

A quantitative (q) PCR mix kit ("Master Mix") (included in the GENEDISC detection kit, available from Pall Corporation, Port Washington, N.Y., USA) is separately prepared for each collection of nucleic acids (a) SEQ ID NOs: 16-18, (b) SEQ ID NOs: 19-21, (c) SEQ ID NOs: 22-24, (d) SEQ ID NOs: 25-27, and (e) SEQ ID NOs: 28-30. The concentration of primers in the PCR reaction mixture is 300 nM and the concentration of probe in the PCR reaction mixture is 200 nM. The barcode located on the GENEDISC plate and the barcode on the identification card contained in the Master Mix bag are scanned using the barcode reader fitted to the GENEDISC cycler (available from Pall Corporation, Port Washington, N.Y., USA). The sample names are entered according to the manufacturer's instructions for the GENE-DISC cycler. The 1.5 mL microtubes corresponding to each of the GENEDISC plate sectors are labeled. The Master Mix is vortexed for 2 seconds, then briefly centrifuged for 2 seconds. Master Mix (6 μL) is added to each microtube. The microtubes are closed. The DNA samples are centrifuged in a bench centrifuge for 15 seconds.

A DNA sample (6 μL) from each species is transferred to the microtube containing the corresponding Master Mix using a pipette. The tube is closed to prevent cross-contamination. The tubes are gently mixed for 2 seconds and then centrifuged for 2 seconds using a mini centrifuge. 12 μL from each microtube is added to the appropriate GENEDISC plate sector. Accordingly, each of (a) SEQ ID NOs: 16-18, (b) SEQ ID NOs: 19-21, (c) SEQ ID NOs: 22-24, (d) SEQ ID NOs: 25-27, and (e) SEQ ID NOs: 28-30, with the corresponding DNA sample, is added to a separate sector of the same GENE-DISC plate.

The GENEDISC plate is loaded. The filling cap is placed on the top of the GENEDISC plate, the cap is gently pressed to ensure that there is no leakage and the vacuum is started. When the GENEDISC cycler indicates that the vacuuming is 90% complete, the GENEDISC plate is tapped to remove any residual bubbles. The cap is removed after the vacuum is released. Mineral oil (4 drops) is loaded into each GENE-DISC plate sector. The filling cap is placed on the GENE-DISC plate and the vacuum is started. The cap is removed at the end of the vacuum cycle and is cleaned by wiping with 70% ethanol. The wells are examined to ensure that there are no partially or unevenly filled wells present that may cause the assay kit to be aborted.

The filling cap is replaced in the designated location. The GENEDISC plate is carefully inserted into the GENEDISC cycler and the lid of the GENEDISC cycler is closed. The PCR is run using the thermal cycling condition. The thermal cycling condition includes four temperatures 112° C., 108°

C., 50° C., and 60° C. The cycling time is 80 seconds per cycle for 45 cycles. At the end of the PCR, the GENEDISC plate is removed and discarded.

The data are analyzed. Real-time PCR data were quantified in terms of cycle threshold (Ct) values. The PCR Efficiency and Linearity are also determined.

NTC measures non-specific signal in the absence of target molecules. As shown in Table 5, the Ct value measured for the NTC is greater than 38, which is considered to be a background signal. Ct values less than 38 are considered positive for the presence of the microorganism. As shown in Table 5, the collections of nucleic acids (a) SEQ ID NOs: 16-18 (AAS), (b) SEQ ID NOs: 19-21 (AAT), (c) SEQ ID NOs: 22-24 (AAP), (d) SEQ ID NOs: 25-27 (ACH), and (e) SEQ ID NOs: 28-30 (AHB) provide a Ct value that is less than that given for the NTC. Therefore, (a) SEQ ID NOs: 16-18, (b) SEQ ID NOs: 19-21, (c) SEQ ID NOs: 22-24, (d) SEQ ID NOs: 25-27, and (e) SEQ ID NOs: 28-30 detect *Alicyclobacillus acidocaldarius, Alicyclobacillus acidoterrestris, Alicyclobacillus acidiphilus, Alicyclobacillus cycloheptanicus*, and *Alicyclobacillus herbarius* DNA, respectively, at 12.5 GU and 25 GU per PCR well. The inhibition control provides a positive PCR signal and measures the degree of PCR inhibition in the presence of sample or contaminant(s) in the sample.

NOs: 16-18, (b) SEQ ID NOs: 19-21, (c) SEQ ID NOs: 22-24, (d) SEQ ID NOs: 25-27, and (e) SEQ ID NOs: 28-30 to detect various amounts of *Alicyclobacillus acidocaldarius, Alicyclobacillus acidoterrestris, Alicyclobacillus acidiphilus, Alicyclobacillus cycloheptanicus*, and *Alicyclobacillus herbarius* DNA (target DNA), respectively. The amounts of target DNA tested were 10,000; 1,000; 100; 50; and 10 GU per PCR well. The results showed that each of (a) SEQ ID NOs: 16-18, (b) SEQ ID NOs: 19-21, (c) SEQ ID NOs: 22-24, (d) SEQ ID NOs: 25-27, and (e) SEQ ID NOs: 28-30 is capable of detecting the respective target DNA at amounts of 10,000; 1,000; 100; 50; and 10 GU per PCR well. Accordingly, the inventive nucleic acids have a limit of detection (LOD) of 10 GU of genomic DNA.

EXAMPLE 3

This example demonstrates the specificity of the inventive nucleic acids.

Genomic DNA is isolated from four spoiling *Alicyclobacillus* species and seven non-spoiler *Alicyclobacillus* species (Table 6), and 15 non-*Alicyclobacillus* species (Table 7) and diluted as described in Example 1. Tris-pH 8.3 buffer (10 mM) is used as a no target control (NTC).

Each of (a) SEQ ID NOs: 16-18, (b) SEQ ID NOs: 19-21, (c) SEQ ID NOs: 22-24, (d) SEQ ID NOs: 25-27, and (e) SEQ

TABLE 5

| Assay Name | NTC Ct | Target DNA at 25 GU/well Ct | Target DNA at 25 GU/well Amplitude | Target DNA at 12.5 GU/well Ct | Target DNA at 12.5 GU/well Amplitude | PCR Efficiency | PCR Linearity |
|---|---|---|---|---|---|---|---|
| AAS | >38 | 30.5 ± 0.97 | 2594 | 31.7 ± 1.03 | 2440 | 95% | 0.999 |
| AAT | >38 | 32.2 ± 0.79 | 2587 | 33.5 ± 0.71 | 2194 | 101% | 0.993 |
| AAP | >38 | 31.5 ± 1.7 | 1990 | 32.3 ± 1.94 | 1550 | 103% | 0.987 |
| ACH | >38 | 32.6 ± 0.75 | 3530 | 32.3 ± 0.91 | 2631 | 101% | 0.995 |
| AHB | >38 | 31.0 ± 0.9 | 4823 | 32.1 ± 1.33 | 4635 | 106% | 0.999 |

EXAMPLE 2

This example demonstrates the sensitivity of the inventive nucleic acids for detecting target *Alicyclobacillus* DNA.

Titration experiments were performed following the procedures of Example 1 to test the ability of each of (a) SEQ ID ID NOs: 28-30 is used to test samples of DNA from each of the microorganisms in Tables 6 and 7 according to the procedures of Example 1. All probes are labeled with 6-FAM fluorescent dye at 5' and BHQ1 quencher at 3' or ROX fluorescent dye at 5' and BHQ2 quencher at 3'.

TABLE 6

| | Ct at 1,000 GU/well DNA | | | | |
|---|---|---|---|---|---|
| Species and Strain No. | SEQ ID NOs: 16-18 | SEQ ID NOs: 22-24 | SEQ ID NOs: 19-21 | SEQ ID NOs: 25-27 | SEQ ID NOs: 28-30 |
| *A. acidiphilus* DSM14558 (S) | 28.0 | 28.5 | >38 | >38 | >38 |
| *A. acidoterrestris* DSM2498 (S) | 28.3 | >38 | 28.1 | >38 | >38 |
| *A. cycloheptanicus* ATCC49029 (S) | 28.3 | >38 | >38 | 26.8 | >38 |
| *A. herbarius* DSM13609 (S) | 27.0 | >38 | >38 | >38 | 26.7 |
| *A. hesperidum* DSM12489 (NS) | 29.0 | >38 | >38 | >38 | >38 |
| *A. acidocaldarius* ATCC43034 (NS) | 27.0 | >38 | >38 | >38 | >38 |
| *A. sendaiensis* ATCC BAA-609 (NS) | 30.0 | >38 | >38 | >38 | >38 |
| *A. tengchongensis* ATCC BAA-2134 (NS) | 29.5 | >38 | >38 | >38 | >38 |
| *A. fastidious* ATCC17978 (NS) | 29.5 | >38 | >38 | >38 | >38 |

TABLE 6-continued

| | Ct at 1,000 GU/well DNA | | | | |
|---|---|---|---|---|---|
| Species and Strain No. | SEQ ID NOs: 16-18 | SEQ ID NOs: 22-24 | SEQ ID NOs: 19-21 | SEQ ID NOs: 25-27 | SEQ ID NOs: 28-30 |
| A. pomorum ATCC14955 (NS) | 29.0 | >38 | >38 | >38 | >38 |
| A. sacchari ATCC17974 (NS) | 29.0 | 38.9 | >38 | >38 | >38 |

S = Spoilage-causing species
NS = Non-spoilage causing species

TABLE 7

| | Assay Ct at 1,000 GU/well DNA | | | | |
|---|---|---|---|---|---|
| Species | SEQ ID NOs: 16-18 | SEQ ID NOs: 22-24 | SEQ ID NOs: 19-21 | SEQ ID NOs: 25-27 | SEQ ID NOs: 28-30 |
| Bacillus subtilis | >38 | >38 | >38 | >38 | >38 |
| Bacillus cereus | >38 | >38 | >38 | >38 | >38 |
| Bacillus mycoides | >38 | >38 | >38 | >38 | >38 |
| Bacillus megaterium | >38 | >38 | >38 | >38 | >38 |
| Burkholderia stabillus | >38 | >38 | >38 | >38 | >38 |
| Megasphaera cerevisiae | >38 | >38 | >38 | >38 | >38 |
| Aspergillus niger | >38 | >38 | >38 | >38 | >38 |
| Moorella thermoacetica | >38 | >38 | >38 | >38 | >38 |
| Lactobacillus brevis | >38 | >38 | >38 | >38 | >38 |
| Lactobacillus casei | >38 | >38 | >38 | >38 | >38 |
| Lactobacillus collinoides | >38 | >38 | >38 | >38 | >38 |
| Lactobacillus coryniformis | >38 | >38 | >38 | >38 | >38 |
| Lactobacillus lindneri | >38 | >38 | >38 | >38 | >38 |
| Candida albicans | >38 | >38 | >38 | >38 | >38 |
| Micrococcus naucinus | >38 | >38 | >38 | >38 | >38 |

As explained in Example 1, the Ct value measured for the NTC is greater than 38, which is considered to be a background signal. Therefore, Ct values less than 38 are considered positive for the presence of the microorganism.

As shown in Tables 6 and 7, each of SEQ ID NOs: 19-21, SEQ ID NOs: 22-24, SEQ ID NOs: 25-27, and SEQ ID NOs: 28-30 specifically detects *Alicyclobacillus acidoterrestris, Alicyclobacillus acidiphilus, Alicyclobacillus cycloheptanicus*, and *Alicyclobacillus herbarius* target DNA, respectively at 1,000 GU per PCR well. However, only background signal is detected in the presence of the non-target *Alicyclobacillus* DNA and the DNA from non-*Alicyclobacillus* species. Accordingly, SEQ ID NOs: 19-21 are highly specific for *Alicyclobacillus acidoterrestris*, SEQ ID NOs: 22-24 are highly specific for *Alicyclobacillus acidiphilus*, SEQ ID NOs: 25-27 are highly specific for *Alicyclobacillus* cycloheptanicus, and SEQ ID NOs: 28-30 are highly specific for *Alicyclobacillus herbarius*.

As shown in Tables 6 and 7, genus-specific SEQ ID NO: 16-18 detected spoiler and non-spoiler *Alicyclobacillus* species DNA at 1,000 GU per PCT well. However, only background signal is detected in the presence of the DNA from non-*Alicyclobacillus* species. Accordingly, SEQ ID NOs: 16-18 are highly specific for the *Alicyclobacillus* genus of microorganisms.

EXAMPLE 4

This example demonstrates the detection of microorganisms within the genus *Alicyclobacillus* generally (*Alicyclobacillus* spp.) as well as the species *Alicyclobacillus acidoterrestris, Alicyclobacillus acidiphilus, Alicyclobacillus cycloheptanicus*, and *Alicyclobacillus herbarius* using the inventive nucleic acids.

The procedures of Example 1 are followed using 1.2 µl of sample DNA from each species in a total volume of 25 µl PCR reaction mixture in a 96-well plate. The negative control was 2.5 µl of water. The PCR is run using the thermal cycling condition on APPLIED BIOSYSTEMS STEPONEPLUS Real-Time PCR System (Carlsbad, Calif.). The thermal cycling condition includes 40 cycles at 95° C. for 15 seconds (denaturation) and 60° C. for 60 seconds (annealing and extension).

The results are consistent with those obtained in Example 1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar references in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of hybridizing a collection of nucleic acids with nucleic acid of *Alicyclobacillus herbarius* in a foodstuff, the method comprising:
   (a) obtaining at least one test sample comprising *Alicyclobacillus herbarius* nucleic acid isolated from foodstuff; and
   (b) contacting the collection of nucleic acids with the at least one test sample under conditions allowing for the collection of nucleic acids to hybridize to the *Alicyclobacillus herbarius* nucleic acid, wherein the collection of nucleic acids comprises:
      (i) a first nucleic acid comprising the nucleotide sequence of SEQ ID NO: 13, 28, 71, or 72 and having a length of no more than 35 nucleotides;
      (ii) a second nucleic acid comprising the nucleotide sequence of SEQ ID NO: 29 or 73 and having a length of no more than 35 nucleotides; and
      (iii) a third nucleic acid comprising the nucleotide sequence of SEQ ID NO: 15 or 30 and having a length of no more than 35 nucleotides.

2. The method according to claim 1, wherein the foodstuff is a beverage.

3. The method according to claim 1, wherein the foodstuff is fruit juice.

4. The method according to claim 1, wherein the collection of nucleic acids is immobilized on a support.

5. The method according to claim 1, wherein one or more of the nucleic acids further comprise a detectable label.

6. The method according to claim 1, wherein the collection of nucleic acids that hybridize to *Alicyclobacillus herbarius* is a first collection of nucleic acids, and the method further comprises hybridizing a second collection of nucleic acids with nucleic acid of *Alicyclobacillus acidoterrestris* in a foodstuff, wherein the method further comprises:
   (a) obtaining at least one test sample comprising *Alicyclobacillus acidoterrestris* nucleic acid isolated from foodstuff; and
   (b) contacting the second collection of nucleic acids with the at least one test sample comprising *Alicyclobacillus acidoterrestris* nucleic acid under conditions allowing for the second collection of nucleic acids to hybridize to the *Alicyclobacillus acidoterrestris* nucleic acid, wherein the second collection of nucleic acids comprises:
      (i) a first nucleic acid selected from the group consisting of SEQ ID NOs: 4, 19, and 42-45 and having a length of no more than 35 nucleotides;
      (ii) a second nucleic acid selected from the group consisting of SEQ ID NOs: 5, 20, and 46-52 and having a length of no more than 35 nucleotides; and
      (iii) a third nucleic acid selected from the group consisting of SEQ ID NOs: 6 and 21 and having a length of no more than 35 nucleotides.

7. The method according to claim 1, wherein the collection of nucleic acids that hybridize to *Alicyclobacillus herbarius* is a first collection of nucleic acids, and the method further comprises hybridizing a second collection of nucleic acids with nucleic acid of *Alicyclobacillus acidiphilus* in a foodstuff; wherein the method further comprises:
   (a) obtaining at least one test sample comprising *Alicyclobacillus acidiphilus* nucleic acid isolated from foodstuff; and
   (b) contacting the second collection of nucleic acids with the at least one test sample comprising *Alicyclobacillus acidiphilus* nucleic acid under conditions allowing for the second collection of nucleic acids to hybridize to the *Alicyclobacillus acidiphilus* nucleic acid, wherein the second collection of nucleic acids comprises:
(i) a first nucleic acid selected from the group consisting of SEQ ID NOs: 7, 22, and 53-57 having a length of no more than 35 nucleotides;
(ii) a second nucleic acid selected from the group consisting of SEQ ID NOs: 8, 23, and 58-66 and having a length of no more than 35 nucleotides; and
(iii) a third nucleic acid selected from the group consisting of SEQ ID NOs: 9 and 24 and having a length of no more than 35 nucleotides.

8. The method according to claim 1, wherein the collection of nucleic acids that hybridize to *Alicyclobacillus herbarius* is a first collection of nucleic acids, and the method further comprises hybridizing a second collection of nucleic acids with nucleic acid of *Alicyclobacillus cycloheptanicus* in a foodstuff, wherein the method further comprises:
(a) obtaining at least one test sample comprising *Alicyclabacillus cycloheptanicus* nucleic acid isolated from foodstuff; and
(b) contacting the second collection of nucleic acids with the at least one test sample comprising *Alicyclobacillus cycloheptanicus* nucleic acid under conditions allowing for the second collection of nucleic acids to hybridize to the *Alicyclobacillus cycloheptanicus* nucleic acid, wherein the second collection of nucleic acids comprises:
(i) a first nucleic acid selected from the group consisting of SEQ ID NOs: 10, 25, and 67 having a length of no more than 35 nucleotides;
(ii) a second nucleic acid selected from the group consisting of SEQ ID NOs: 11, 26, and 68-70 and having a length of no more than 35 nucleotides; and
(iii) a third nucleic acid selected from the group consisting of SEQ ID NOs: 12 and 27 and having a length of no more than 35 nucleotides.

9. The method according to claim 1, wherein the collection of nucleic acids that hybridize to *Alicyclobacillus herbarius* is a first collection of nucleic acids, the test sample comprising *Alicyclobacillus herbarius* is a first test sample, and the method further comprises hybridizing a second collection of nucleic acids with nucleic acid of *Alicyclobacillus* in a foodstuff, wherein the method further comprises:
(a) obtaining a second test sample comprising *Alicyclobacillus* nucleic acid isolated from foodstuff; and
(b) contacting the second collection of nucleic acids with the second test sample under conditions allowing for the second collection of nucleic acids to hybridize to the *Alicyclobacillus* nucleic acid, wherein the second collection of nucleic acids comprises:
(i) a first nucleic acid selected from the group consisting of SEQ ID NOs: 1, 16, and 31-34 having a length of no more than 35 nucleotides;
(ii) a second nucleic acid selected from the group consisting of SEQ ID NOs: 2, 17, and 35-41 and having a length of no more than 35 nucleotides; and
(iii) a third nucleic acid selected from the group consisting of SEQ ID NOs: 3 and 18 and having a length of no more than 35 nucleotides.

10. The method according to claim 1, wherein the collection of nucleic acids comprises:
(i) a first nucleic acid comprising the nucleotide sequence of SEQ ID NO: 13, 28, 71, or 72 and having a length of no more than 30 nucleotides;
(ii) a second nucleic acid comprising the nucleotide sequence of SEQ ID NO: 29 or 73 and having a length of no more than 30 nucleotides; and
(iii) a third nucleic acid comprising the nucleotide sequence of SEQ ID NO: 15 or 30 and having a length of no more than 30 nucleotides.

11. The method according to claim 10, wherein the collection of nucleic acids is immobilized on a support.

12. The method according to claim 10, wherein one or more of the nucleic acids further comprise a detectable label.

13. The method according to claim 1, wherein the collection of nucleic acids comprises:
(i) a first nucleic acid comprising the nucleotide sequence of SEQ ID NO: 13, 28, 71, or 72 and having a length of no more than 25 nucleotides;
(ii) a second nucleic acid comprising the nucleotide sequence of SEQ ID NO: 29 or 73 and having a length of no more than 25 nucleotides; and
(iii) a third nucleic acid comprising the nucleotide sequence of SEQ ID NO: 15 or 30 and having a length of no more than 25 nucleotides.

14. The method according to claim 13, wherein the collection of nucleic acids is immobilized on a support.

15. The method according to claim 13, wherein one or more of the nucleic acids further comprise a detectable label.

16. The method according to claim 1, wherein the collection of nucleic acids comprises:
(i) a first nucleic acid comprising the nucleotide sequence of SEQ ID NO: 13, 28, 71, or 72 and having a length of no more than 18 nucleotides;
(ii) a second nucleic acid comprising the nucleotide sequence of SEQ ID NO: 29 or 73 and having a length of no more than 18 nucleotides; and
(iii) a third nucleic acid comprising the nucleotide sequence of SEQ ID NO: 15 or 30 and having a length of no more than 25 nucleotides.

17. The method according to claim 16, wherein the collection of nucleic acids is immobilized on a support.

18. The method according to claim 16, wherein one or more of the nucleic acids further comprise a detectable label.

19. The method according to claim 1, wherein the collection of nucleic acids comprises:
(i) a first nucleic acid consisting of SEQ ID NO: 13, 28, 71, or 72,
(ii) a second nucleic acid consisting of the nucleotide sequence of SEQ ID NO: 29 or 73, and
(iii) a third nucleic acid consisting of the nucleotide sequence of SEQ ID NO: 15 or 30.

* * * * *

```
                          SEQUENCE LISTING

<160> NUMBER OF SEQ ID NOS: 74

<210> SEQ ID NO 1
<211> LENGTH: 15
<212> TYPE: DNA
<213> ORGANISM: Artificial Sequence
<220> FEATURE:
<223> OTHER INFORMATION: Synthetic

<400> SEQUENCE: 1
tggacagtga ctgac                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
gcttattggg tttcc                                                      15

<210> SEQ ID NO 3
<211> LENGTH: 15
<212> TYPE: DNA
<213> ORGANISM: Artificial Sequence
<220> FEATURE:
<223> OTHER INFORMATION: Synthetic

<400> SEQUENCE: 3
cgtaaacgat gagtg                                                      15

<210> SEQ ID NO 4
<211> LENGTH: 15
<212> TYPE: DNA
<213> ORGANISM: Artificial Sequence
<220> FEATURE:
<223> OTHER INFORMATION: Synthetic

<400> SEQUENCE: 4
aatctgcctt tcaga                                                      15

<210> SEQ ID NO 5
<211> LENGTH: 15
<212> TYPE: DNA
<213> ORGANISM: Artificial Sequence
<220> FEATURE:
<223> OTHER INFORMATION: Synthetic

<400> SEQUENCE: 5
tctttcaaca caaat                                                      15
```

```
<210> SEQ ID NO 6
<211> LENGTH: 15
<212> TYPE: DNA
<213> ORGANISM: Artificial Sequence
<220> FEATURE:
<223> OTHER INFORMATION: Synthetic

<400> SEQUENCE: 6
attatccggc attag                                                          15

<210> SEQ ID NO 7
<211> LENGTH: 15
<212> TYPE: DNA
<213> ORGANISM: Artificial Sequence
<220> FEATURE:
<223> OTHER INFORMATION: Synthetic

<400> SEQUENCE: 7
cgttgtccgg aatca                                                          15

<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8
gtttccaaag acaaa                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
acttacacaa ccgcc                                                          15

<210> SEQ ID NO 10
<211> LENGTH: 15
<212> TYPE: DNA
<213> ORGANISM: Artificial Sequence
<220> FEATURE:
<223> OTHER INFORMATION: Synthetic

<400> SEQUENCE: 10
tgggaaaggt gcaag                                                          15

<210> SEQ ID NO 11
<211> LENGTH: 15
<212> TYPE: DNA
<213> ORGANISM: Artificial Sequence
<220> FEATURE:
<223> OTHER INFORMATION: Synthetic

<400> SEQUENCE: 11
tcgtcgcctt ggtga                                                          15

<210> SEQ ID NO 12
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 12
cgcagatgga ggagc                                              15

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
acaccacgag agtga                                              15

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
gcggctggct cctat                                              15

<210> SEQ ID NO 15
<211> LENGTH: 15
<212> TYPE: DNA
<213> ORGANISM: Artificial Sequence
<220> FEATURE:
<223> OTHER INFORMATION: Synthetic

<400> SEQUENCE: 15
cgaagtcggt gaggc                                              15

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
cttgctggac agtgactgac                                         20

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
cccggagtgc ttattgggtt tcc                                     23

<210> SEQ ID NO 18
<211> LENGTH: 28
<212> TYPE: DNA
<213> ORGANISM: Artificial Sequence
<220> FEATURE:
<223> OTHER INFORMATION: Synthetic

<400> SEQUENCE: 18
ccacgccgta aacgatgagt gctaggtg                                28

<210> SEQ ID NO 19
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 19
ggggcaatct gcctttcaga                                                     20

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
cagttgcatc tttcaacaca aat                                                 23

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
cccgtgtatt atccggcatt agcacccgt                                           29

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
cgcaagcgtt gtccggaatc a                                                   21

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23
aagttatgca gtttccaaag acaaa                                               25

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
actccagact tacacaaccg cctacgca                                            28

<210> SEQ ID NO 25
<211> LENGTH: 17
<212> TYPE: DNA
<213> ORGANISM: Artificial Sequence
<220> FEATURE:
<223> OTHER INFORMATION: Synthetic

<400> SEQUENCE: 25
```
gctgggaaag gtgcaag                                                   17

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
ggcatcgtcg ccttggtga                                                 19

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
caccgcagat ggaggagccc gc                                             22

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
gtcacaccac gagagtga                                                  18

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
cgggcggctg gctcctat                                                  18

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30
acacccgaag tcggtgaggc aaccg                                          25

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
ttgctggaca gtgactgac                                                 19

<210> SEQ ID NO 32
<211> LENGTH: 18
<212> TYPE: DNA

```
<213> ORGANISM: Artificial Sequence
<220> FEATURE:
<223> OTHER INFORMATION: Synthetic

<400> SEQUENCE: 32
tgctggacag tgactgac                                                 18

<210> SEQ ID NO 33
<211> LENGTH: 17
<212> TYPE: DNA
<213> ORGANISM: Artificial Sequence
<220> FEATURE:
<223> OTHER INFORMATION: Suntthetic

<400> SEQUENCE: 33
gctggacagt gactgac                                                  17

<210> SEQ ID NO 34
<211> LENGTH: 16
<212> TYPE: DNA
<213> ORGANISM: Artificial Sequence
<220> FEATURE:
<223> OTHER INFORMATION: Synthetic

<400> SEQUENCE: 34
ctggacagtg actgac                                                   16

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
ccggagtgct tattgggttt cc                                            22

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
cggagtgctt attgggtttc c                                             21

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ggagtgctta tgggtttcc                                                20

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
gagtgcttat tgggtttcc                                                19
```

<210> SEQ ID NO 39
<211> LENGTH: 18
<212> TYPE: DNA
<213> ORGANISM: Artificial Sequence
<220> FEATURE:
<223> OTHER INFORMATION: Synthetic

<400> SEQUENCE: 39
agtgcttatt gggtttcc                                                    18

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
gtgcttattg ggtttcc                                                     17

<210> SEQ ID NO 41
<211> LENGTH: 16
<212> TYPE: DNA
<213> ORGANISM: Artificial Sequence
<220> FEATURE:
<223> OTHER INFORMATION: Synthetic

<400> SEQUENCE: 41
tgcttattgg gtttcc                                                      16

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
gggcaatctg cctttcaga                                                   19

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
ggcaatctgc ctttcaga                                                    18

<210> SEQ ID NO 44
<211> LENGTH: 17
<212> TYPE: DNA
<213> ORGANISM: Artificial Sequence
<220> FEATURE:
<223> OTHER INFORMATION: Synthetic

<400> SEQUENCE: 44
gcaatctgcc tttcaga                                                     17

<210> SEQ ID NO 45
<211> LENGTH: 16
<212> TYPE: DNA
<213> ORGANISM: Artificial Sequence
<220> FEATURE:

```
<223> OTHER INFORMATION: Synthetic

<400> SEQUENCE: 45
caatctgcct ttcaga                                                        16

<210> SEQ ID NO 46
<211> LENGTH: 22
<212> TYPE: DNA
<213> ORGANISM: Artificial Sequence
<220> FEATURE:
<223> OTHER INFORMATION: Synthetic

<400> SEQUENCE: 46
agttgcatct ttcaacacaa at                                                 22

<210> SEQ ID NO 47
<211> LENGTH: 21
<212> TYPE: DNA
<213> ORGANISM: Artificial Sequence
<220> FEATURE:
<223> OTHER INFORMATION: Synthetic

<400> SEQUENCE: 47
gttgcatctt tcaacacaaa t                                                  21

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ttgcatcttt caacacaaat                                                    20

<210> SEQ ID NO 49
<211> LENGTH: 19
<212> TYPE: DNA
<213> ORGANISM: Artificial Sequence
<220> FEATURE:
<223> OTHER INFORMATION: Synthetic

<400> SEQUENCE: 49
tgcatctttc aacacaaat                                                     19

<210> SEQ ID NO 50
<211> LENGTH: 18
<212> TYPE: DNA
<213> ORGANISM: Artificial Sequence
<220> FEATURE:
<223> OTHER INFORMATION: Synthetic

<400> SEQUENCE: 50
gcatctttca acacaaat                                                      18

<210> SEQ ID NO 51
<211> LENGTH: 17
<212> TYPE: DNA
<213> ORGANISM: Artificial Sequence
<220> FEATURE:
<223> OTHER INFORMATION: Synthetic

<400> SEQUENCE: 51
catctttcaa cacaaat                                                       17
```

```
<210> SEQ ID NO 52
<211> LENGTH: 16
<212> TYPE: DNA
<213> ORGANISM: Artificial Sequence
<220> FEATURE:
<223> OTHER INFORMATION: Synthetic

<400> SEQUENCE: 52
atctttcaac acaaat                                              16

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gcaagcgttg tccggaatca                                          20

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
caagcgttgt ccggaatca                                           19

<210> SEQ ID NO 55
<211> LENGTH: 18
<212> TYPE: DNA
<213> ORGANISM: Artificial Sequence
<220> FEATURE:
<223> OTHER INFORMATION: Synthetic

<400> SEQUENCE: 55
aagcgttgtc cggaatca                                            18

<210> SEQ ID NO 56
<211> LENGTH: 17
<212> TYPE: DNA
<213> ORGANISM: Artificial Sequence
<220> FEATURE:
<223> OTHER INFORMATION: Synthetic

<400> SEQUENCE: 56
agcgttgtcc ggaatca                                             17

<210> SEQ ID NO 57
<211> LENGTH: 16
<212> TYPE: DNA
<213> ORGANISM: Artificial Sequence
<220> FEATURE:
<223> OTHER INFORMATION: Synthetic

<400> SEQUENCE: 57
gcgttgtccg gaatca                                              16

<210> SEQ ID NO 58
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 58
agttatgcag tttccaaaga caaa                                          24

<210> SEQ ID NO 59
<211> LENGTH: 23
<212> TYPE: DNA
<213> ORGANISM: Artificial Sequence
<220> FEATURE:
<223> OTHER INFORMATION: Synthetic

<400> SEQUENCE: 59
gttatgcagt ttccaaagac aaa                                           23

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
ttatgcagtt tccaaagaca aa                                            22

<210> SEQ ID NO 61
<211> LENGTH: 21
<212> TYPE: DNA
<213> ORGANISM: Artificial Sequence
<220> FEATURE:
<223> OTHER INFORMATION: Synthetic

<400> SEQUENCE: 61
tatgcagttt ccaaagacaa a                                             21

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
atgcagtttc caaagacaaa                                               20

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
tgcagtttcc aaagacaaa                                                19

<210> SEQ ID NO 64
<211> LENGTH: 18
<212> TYPE: DNA
<213> ORGANISM: Artificial Sequence
<220> FEATURE:
<223> OTHER INFORMATION: Synthetic

<400> SEQUENCE: 64
gcagtttcca aagacaaa                                                 18

<210> SEQ ID NO 65
<211> LENGTH: 17
```

```
<212> TYPE: DNA
<213> ORGANISM: Artificial Sequence
<220> FEATURE:
<223> OTHER INFORMATION: Synthetic

<400> SEQUENCE: 65
cagtttccaa agacaaa                                                    17

<210> SEQ ID NO 66
<211> LENGTH: 16
<212> TYPE: DNA
<213> ORGANISM: Artificial Sequence
<220> FEATURE:
<223> OTHER INFORMATION: Synthetic

<400> SEQUENCE: 66
agtttccaaa gacaaa                                                     16

<210> SEQ ID NO 67
<211> LENGTH: 16
<212> TYPE: DNA
<213> ORGANISM: Artificial Sequence
<220> FEATURE:
<223> OTHER INFORMATION: Synthetic

<400> SEQUENCE: 67
ctgggaaagg tgcaag                                                     16

<210> SEQ ID NO 68
<211> LENGTH: 18
<212> TYPE: DNA
<213> ORGANISM: Artificial Sequence
<220> FEATURE:
<223> OTHER INFORMATION: Synthetic

<400> SEQUENCE: 68
gcatcgtcgc cttggtga                                                   18

<210> SEQ ID NO 69
<211> LENGTH: 17
<212> TYPE: DNA
<213> ORGANISM: Artificial Sequence
<220> FEATURE:
<223> OTHER INFORMATION: Synthetic

<400> SEQUENCE: 69
catcgtcgcc ttggtga                                                    17

<210> SEQ ID NO 70
<211> LENGTH: 16
<212> TYPE: DNA
<213> ORGANISM: Artificial Sequence
<220> FEATURE:
<223> OTHER INFORMATION: Synthetic

<400> SEQUENCE: 70
atcgtcgcct tggtga                                                     16

<210> SEQ ID NO 71
<211> LENGTH: 17
<212> TYPE: DNA
<213> ORGANISM: Artificial Sequence
<220> FEATURE:
<223> OTHER INFORMATION: Synthetic

<400> SEQUENCE: 71
```

-continued

```
tcacaccacg agagtga                                            17

<210> SEQ ID NO 72
<211> LENGTH: 16
<212> TYPE: DNA
<213> ORGANISM: Artificial Sequence
<220> FEATURE:
<223> OTHER INFORMATION: Synthetic

<400> SEQUENCE: 72
cacaccacga gagtga                                             16

<210> SEQ ID NO 73
<211> LENGTH: 17
<212> TYPE: DNA
<213> ORGANISM: Artificial Sequence
<220> FEATURE:
<223> OTHER INFORMATION: Synthetic

<400> SEQUENCE: 73
gggcggctgg ctcctat                                            17

<210> SEQ ID NO 74
<211> LENGTH: 16
<212> TYPE: DNA
<213> ORGANISM: Artificial Sequence
<220> FEATURE:
<223> OTHER INFORMATION: Synthetic

<400> SEQUENCE: 74
ggcggctggc tcctat                                             16
```